(12) United States Patent
Robertson et al.

(10) Patent No.: US 11,744,699 B2
(45) Date of Patent: *Sep. 5, 2023

(54) HEART VALVE PROSTHESES AND METHODS FOR PERCUTANEOUS HEART VALVE REPLACEMENT

(71) Applicant: Medtronic Vascular, Inc., Santa Rosa, CA (US)

(72) Inventors: Scott Robertson, San Francisco, CA (US); Elliot Howard, Aliso Viejo, CA (US)

(73) Assignee: MEDTRONIC VASCULAR, INC., Santa Rosa, CA (US)

(*) Notice: Subject to any disclaimer, the term of this patent is extended or adjusted under 35 U.S.C. 154(b) by 6 days.

This patent is subject to a terminal disclaimer.

(21) Appl. No.: 16/665,029

(22) Filed: Oct. 28, 2019

(65) Prior Publication Data

US 2020/0121453 A1   Apr. 23, 2020

Related U.S. Application Data

(63) Continuation of application No. 14/879,861, filed on Oct. 9, 2015, now Pat. No. 10,456,243.

(51) Int. Cl.
*A61F 2/06* (2013.01)
*A61F 2/24* (2006.01)

(52) U.S. Cl.
CPC .......... *A61F 2/2403* (2013.01); *A61F 2/2409* (2013.01); *A61F 2/2418* (2013.01);
(Continued)

(58) Field of Classification Search
CPC ............ A61F 2/2418; A61F 2210/0014; A61F 2220/0008; A61F 2/2427; A61F 2/2409;
(Continued)

(56) References Cited

U.S. PATENT DOCUMENTS 7,748,389 B2   7/2010   Salahieh et al.
7,837,727 B2   11/2010   Goetz et al.
(Continued)

FOREIGN PATENT DOCUMENTS

DE   10 2006 052 564 B3   12/2007
DE   10 2008 015 781 A1   10/2009
(Continued)

OTHER PUBLICATIONS

International Search Report and Written Opinion dated Jan. 3, 2017 in corresponding International Patent Application No. PCT/US2016/055585.

(Continued)

*Primary Examiner* — Ann Schillinger
(74) *Attorney, Agent, or Firm* — MEDLER FERRO WOODHOUSE & MILLS PLLC

(57) ABSTRACT

Prosthetic heart valve devices and associated methods for percutaneous heart valve replacement are disclosed herein. A transcatheter valve prosthesis configured in accordance herewith includes a frame having a valve support and one or more support arms coupled thereto. The one or more support arms are configured to extend from the second end of the valve support toward the first end when the valve prosthesis is in an expanded configuration. When deployed in the expanded configuration, the one or more support arms have a curvilinear shape, such as a substantially S-shape, that at least partially engages tissue at the native heart valve.

7 Claims, 13 Drawing Sheets

(52) U.S. Cl.
CPC ... *A61F 2230/001* (2013.01); *A61F 2230/005* (2013.01); *A61F 2230/0028* (2013.01); *A61F 2230/0069* (2013.01)

(58) Field of Classification Search
CPC ...... A61F 2/246; A61F 2/2457; A61F 2/2412; A61F 2/24; A61F 2/2463; A61F 2/2403; A61F 2230/001; A61F 2230/005; A61F 2230/0028; A61F 2230/0069
See application file for complete search history.

(56) References Cited

U.S. PATENT DOCUMENTS

| | | | |
|---|---|---|---|
| 7,896,915 | B2 | 3/2011 | Guyenot et al. |
| 7,914,575 | B2 | 3/2011 | Geyenot et al. |
| 7,947,075 | B2 | 5/2011 | Goetz et al. |
| 7,972,378 | B2 | 7/2011 | Tabor et al. |
| 8,052,749 | B2 | 11/2011 | Salahieh et al. |
| 8,343,213 | B2 | 1/2013 | Salahieh et al. |
| 8,348,995 | B2 | 1/2013 | Tuval et al. |
| 8,348,996 | B2 | 1/2013 | Tuval et al. |
| 8,366,767 | B2 | 2/2013 | Zhang |
| 8,366,768 | B2 | 2/2013 | Zhang |
| 8,398,708 | B2 | 3/2013 | Meiri et al. |
| 8,414,643 | B2 | 4/2013 | Tuval et al. |
| 8,444,689 | B2 | 5/2013 | Zhang |
| 8,449,599 | B2 | 5/2013 | Chau et al. |
| 8,540,767 | B2 | 9/2013 | Zhang |
| 8,579,964 | B2 | 11/2013 | Lane et al. |
| 8,579,965 | B2 | 11/2013 | Bonhoeffer et al. |
| 8,585,755 | B2 | 11/2013 | Chau et al. |
| 8,673,000 | B2 | 3/2014 | Tabor et al. |
| 8,728,155 | B2 * | 5/2014 | Montorfano .......... A61F 2/2409 623/2.37 |
| 8,747,460 | B2 | 6/2014 | Tuval et al. |
| 8,771,345 | B2 | 7/2014 | Tuval et al. |
| 8,771,346 | B2 | 7/2014 | Tuval et al. |
| 8,784,481 | B2 | 7/2014 | Alkhatib et al. |
| 8,834,563 | B2 | 9/2014 | Righini |
| 8,834,564 | B2 | 9/2014 | Tuval et al. |
| 8,840,661 | B2 | 9/2014 | Manasse |
| 8,876,894 | B2 | 11/2014 | Tuval et al. |
| 8,876,895 | B2 | 11/2014 | Tuval et al. |
| 8,926,691 | B2 | 1/2015 | Chau et al. |
| 8,956,404 | B2 | 2/2015 | Bortlein et al. |
| 8,986,373 | B2 | 3/2015 | Chau et al. |
| 8,992,604 | B2 | 3/2015 | Gross et al. |
| 9,125,740 | B2 * | 9/2015 | Morriss ................. A61F 2/2418 |
| 9,295,552 | B2 | 3/2016 | McLean et al. |
| 9,763,780 | B2 * | 9/2017 | Morriss ................. A61F 2/2418 |
| 10,456,243 | B2 * | 10/2019 | Robertson ............ A61F 2/2418 |
| 10,583,000 | B2 * | 3/2020 | Ratz ...................... A61F 2/2409 |
| 2003/0036791 | A1 | 2/2003 | Bonhoeffer et al. |
| 2004/0210304 | A1 | 10/2004 | Seguin et al. |
| 2006/0020333 | A1 | 1/2006 | Lashinski et al. |
| 2009/0112309 | A1 | 4/2009 | Jaramillo et al. |
| 2009/0216312 | A1 | 8/2009 | Straubinger et al. |
| 2010/0094411 | A1 | 4/2010 | Tuval et al. |
| 2010/0131054 | A1 | 5/2010 | Tuval et al. |
| 2010/0137979 | A1 | 6/2010 | Tuval et al. |
| 2010/0268332 | A1 | 10/2010 | Tuval et al. |
| 2011/0137397 | A1 * | 6/2011 | Chau ..................... A61F 2/24 623/1.11 |
| 2011/0208297 | A1 | 8/2011 | Tuval et al. |
| 2011/0224785 | A1 | 9/2011 | Hacohen |
| 2012/0022640 | A1 * | 1/2012 | Gross .................... A61F 2/243 623/2.11 |
| 2012/0035722 | A1 | 2/2012 | Tuval |
| 2012/0053682 | A1 | 3/2012 | Kovalsky et al. |
| 2012/0078360 | A1 | 3/2012 | Rafiee |
| 2012/0185039 | A1 | 7/2012 | Tuval et al. |
| 2012/0303116 | A1 | 11/2012 | Gorman, III et al. |
| 2013/0116779 | A1 | 5/2013 | Weber |
| 2013/0172992 | A1 * | 7/2013 | Gross ..................... A61F 2/2436 623/2.11 |
| 2013/0190861 | A1 | 7/2013 | Chau et al. |
| 2013/0310928 | A1 | 11/2013 | Morriss et al. |
| 2014/0018906 | A1 * | 1/2014 | Rafiee ..................... A61F 2/2427 623/1.26 |
| 2014/0039611 | A1 | 2/2014 | Lane et al. |
| 2014/0039613 | A1 | 2/2014 | Navia et al. |
| 2014/0046434 | A1 * | 2/2014 | Rolando ................. A61F 2/2418 623/2.11 |
| 2014/0052237 | A1 | 2/2014 | Lane et al. |
| 2014/0052240 | A1 | 2/2014 | Zhang |
| 2014/0067054 | A1 * | 3/2014 | Chau ...................... A61F 2/2436 623/2.36 |
| 2014/0088695 | A1 | 3/2014 | Figulla et al. |
| 2014/0088696 | A1 * | 3/2014 | Figulla .................. A61F 2/2412 623/2.17 |
| 2014/0121763 | A1 | 5/2014 | Duffy et al. |
| 2014/0155997 | A1 | 6/2014 | Braido |
| 2014/0194982 | A1 | 7/2014 | Kovalsky et al. |
| 2014/0194983 | A1 | 7/2014 | Kovalsky et al. |
| 2014/0207231 | A1 | 7/2014 | Hacohen et al. |
| 2014/0222136 | A1 * | 8/2014 | Geist ...................... A61F 2/2412 623/2.37 |
| 2014/0222142 | A1 | 8/2014 | Kovalsky et al. |
| 2014/0228946 | A1 | 8/2014 | Chau et al. |
| 2014/0236292 | A1 | 8/2014 | Braido |
| 2014/0249622 | A1 * | 9/2014 | Carmi ................... A61F 2/2418 623/2.11 |
| 2014/0257467 | A1 | 9/2014 | Lane et al. |
| 2014/0277390 | A1 | 9/2014 | Ratz et al. |
| 2014/0277409 | A1 | 9/2014 | Bortlein et al. |
| 2014/0277410 | A1 | 9/2014 | Bortlein et al. |
| 2014/0277411 | A1 | 9/2014 | Bortlein et al. |
| 2014/0324164 | A1 | 10/2014 | Gross et al. |
| 2014/0343669 | A1 | 11/2014 | Lane et al. |
| 2014/0350669 | A1 | 11/2014 | Gillespie et al. |
| 2014/0371844 | A1 | 12/2014 | Dale et al. |
| 2014/0379074 | A1 * | 12/2014 | Spence ................. A61F 2/2409 623/2.11 |
| 2015/0018944 | A1 | 1/2015 | O'Connell et al. |
| 2015/0073540 | A1 | 3/2015 | Salahieh et al. |
| 2015/0073541 | A1 | 3/2015 | Salahieh et al. |
| 2015/0081013 | A1 | 3/2015 | Braido et al. |
| 2015/0119982 | A1 | 4/2015 | Quill et al. |
| 2015/0351904 | A1 * | 12/2015 | Cooper ................ A61F 2/2418 623/2.1 |
| 2015/0359631 | A1 | 12/2015 | Sheahan et al. |
| 2017/0143486 | A1 * | 5/2017 | Zeng .................... A61F 2/2412 |

FOREIGN PATENT DOCUMENTS

| | | | | |
|---|---|---|---|---|
| EP | 1 472 996 | A1 | 11/2004 | |
| EP | 2 495 055 | A1 | 9/2012 | |
| EP | 2777615 | A1 * | 9/2014 | .......... A61F 2/2409 |
| JP | 2014-522678 | A | 9/2014 | |
| JP | 2014552678 | A | 9/2014 | |
| WO | 2005/062980 | A2 | 7/2005 | |
| WO | 2009/033914 | A1 | 3/2009 | |
| WO | 2009/108615 | A1 | 9/2009 | |
| WO | 2011/057087 | A1 | 5/2011 | |
| WO | 2011/069048 | A2 | 6/2011 | |
| WO | 2011/111047 | A2 | 9/2011 | |
| WO | 2011/137531 | A1 | 11/2011 | |
| WO | 2011/163275 | A2 | 12/2011 | |
| WO | 2012/061809 | A2 | 5/2012 | |
| WO | 2012/085913 | A2 | 6/2012 | |
| WO | 2012/095159 | A2 | 7/2012 | |
| WO | 20120177942 | A2 | 12/2012 | |
| WO | WO2012/177942 | | 12/2012 | |
| WO | 2013/021374 | A2 | 2/2013 | |
| WO | 2013/059747 | A1 | 4/2013 | |
| WO | 2013/072496 | A1 | 5/2013 | |
| WO | 2013/086413 | A1 | 6/2013 | |
| WO | 2013/114214 | A2 | 8/2013 | |
| WO | 2013/155970 | A1 | 10/2013 | |
| WO | 2013/175468 | A2 | 11/2013 | |
| WO | 2013/177684 | A1 | 12/2013 | |
| WO | 2014/121275 | A1 | 8/2014 | |
| WO | 20140170463 | A1 | 10/2014 | |

(56) References Cited

FOREIGN PATENT DOCUMENTS

| WO | 2015/061378 A1 | 4/2015 | | |
| WO | WO-2016149453 A1 * | 9/2016 | ........... | A61F 2/2409 |
| WO | WO-2017035487 A1 * | 3/2017 | ........... | A61F 2/2418 |

OTHER PUBLICATIONS

Office Action dated Nov. 29, 2022 in Japanese Appl. No. 2022-014706 (with English translation).

* cited by examiner

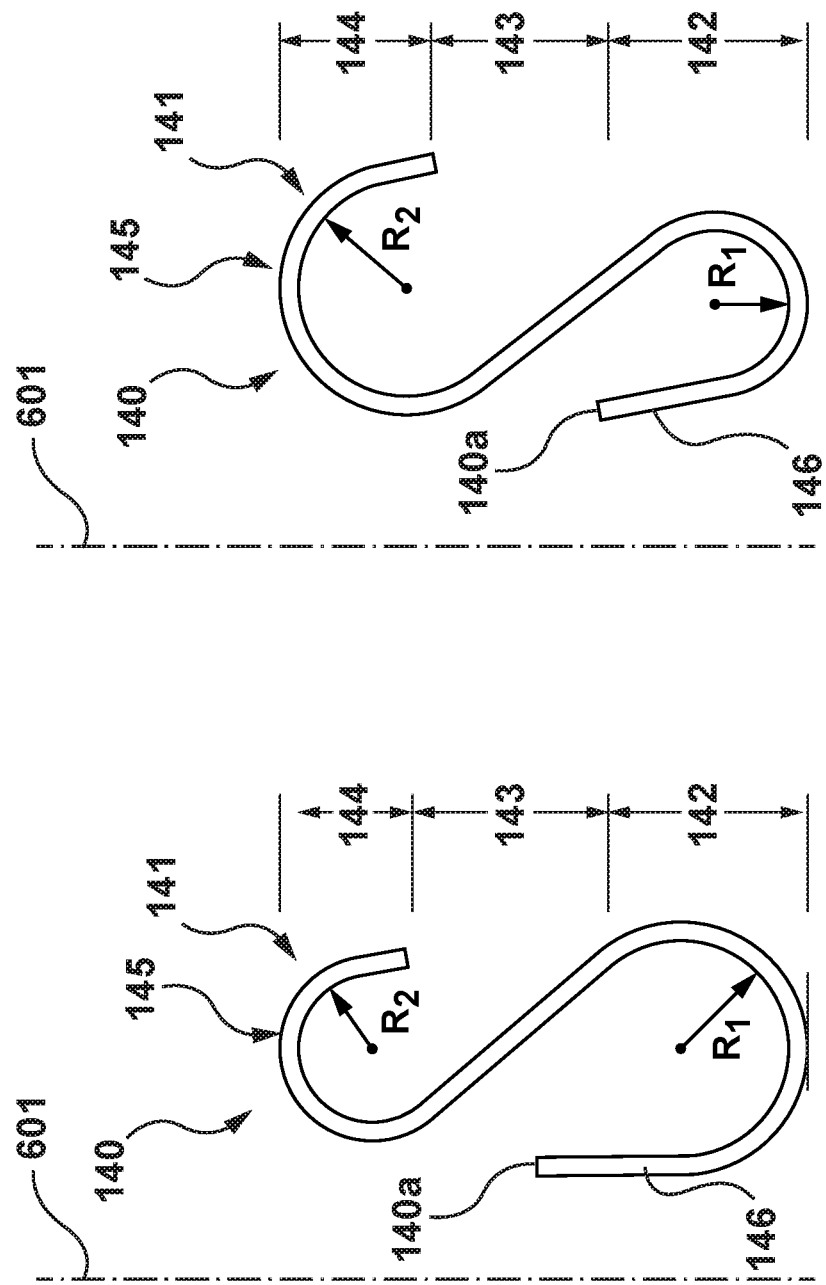

HEART VALVE PROSTHESES AND METHODS FOR PERCUTANEOUS HEART VALVE REPLACEMENT

CROSS-REFERENCE TO RELATED APPLICATIONS

This application is a continuation of prior U.S. application Ser. No. 14/879,861, filed on Oct. 9, 2015, now U.S. Pat. No. 10,456,243, which is hereby incorporated by reference in its entirety for all purposes.

FIELD OF THE INVENTION

The present technology relates generally to heart valve prostheses and associated methods. In particular, several embodiments are directed to transcatheter heart valve devices for percutaneous replacement of native heart valves, such as a mitral valve.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To insure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber to occur at the proper flow rate and cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Prosthetic heart valves have been developed for repair and replacement of diseased and/or damaged heart valves. Such valves can be percutaneously delivered and deployed at the site of the diseased heart valve through catheter-based systems. Such prosthetic heart valves can be delivered while in a low-profile or compressed/contracted arrangement so that the prosthetic valves can be contained within a sheath component of a delivery catheter and advanced through the patient's vasculature. Once positioned at the treatment site, the prosthetic valves can be expanded to engage tissue at the diseased heart valve region to, for instance, hold the prosthetic valve in position. While these prosthetic valves offer minimally invasive methods for heart valve repair and/or replacement, challenges remain to provide prosthetic valves that prevent leakage between the implanted prosthetic valve and the surrounding tissue (paravalvular leakage) and for preventing movement and/or migration of the prosthetic valve that could occur during the cardiac cycle. For example, the mitral valve presents numerous challenges, such as prosthetic valve dislodgement or improper placement due to the presence of chordae tendinae and remnant leaflets, leading to valve impingement. Additional challenges can include providing a prosthetic valve that resists pre-mature failure of various components that can occur when subjected to the distorting forces imparted by the native anatomy and during the cardiac cycle. Further anatomical challenges associated with treatment of a mitral valve include providing a prosthetic valve to accommodate the oval or kidney shape. Moreover, the kidney-shaped mitral valve annulus has muscle only along the exterior wall of the valve with only a thin vessel wall that separates the mitral valve and the aortic valve. This anatomical muscle distribution, along with the high pressures experienced on the left ventricular contraction, can be problematic for mitral valve prosthesis.

BRIEF SUMMARY OF THE INVENTION

Embodiments hereof are directed to heart valve prostheses and methods of percutaneous implantation thereof. The heart valve prostheses have a compressed configuration for delivery via a vasculature or other body lumens to a native heart valve of a patient and an expanded configuration for deployment within the native heart valve. In an embodiment, the heart valve prosthesis may include a frame having a valve support that is configured to hold a prosthetic valve component therein, and a plurality of support arms extending from the valve support such that when the heart valve prosthesis is in the expanded configuration the plurality of support arms are configured to extend toward the first end of the valve support for engaging a subannular surface of the native heart valve. One or more of the plurality of support arms comprises a curvilinear-shaped support arm, the curvilinear-shaped support arm being formed to have opposing first and second arcuate regions longitudinally separated by a straight region extending therebetween, with the first arcuate region being formed to curve toward the valve support proximate a downstream portion thereof, the straight region being formed to slant toward the valve support while joining the first arcuate region and the second arcuate region, and the second arcuate region being formed to curve away from the valve support proximate an upstream portion thereof.

In another embodiment, a heart valve prosthesis for implantation at a native valve region of a heart includes a valve support having an upstream portion and a downstream portion, the valve support being configured to retain a prosthetic valve component therein and having a plurality of support arms extending from the downstream portion of the valve support. When the heart valve prosthesis is in an expanded configuration, each support arm is configured to extend from the downstream portion toward the upstream portion and to have a curvilinear shape with a first curved region having a first radius of curvature, a second curved region having a second radius of curvature and an elongate region extending between the first curved region and the second curved region. In such supports arms, the curvilinear shape is configured to absorb distorting forces exerted thereon by the native valve region.

In another embodiment, a heart valve prosthesis for treating a native mitral valve of a patient is disclosed. The heart valve prosthesis includes a cylindrical support having an upstream portion, a downstream portion and a first cross-sectional dimension, wherein the cylindrical support is configured to hold a prosthetic valve component that inhibits retrograde blood flow. A plurality of S-shaped support arms extend from the downstream portion of the cylindrical support, such that when the heart valve prosthesis is in an expanded configuration the S-shaped support arms are configured to extend in an upstream direction to engage cardiac tissue on or below an annulus of the native mitral valve. A radially-extending segment extends from the upstream portion of the cylindrical support and is of a second cross-sectional dimension greater than the first cross-sectional dimension. The radially-extending segment is configured to engage cardiac tissue on or above the annulus of the native mitral valve such that when the heart valve prosthesis is in the expanded configuration and deployed at the native mitral valve, the annulus is positioned between upstream curved segments of the S-shaped support arms and the radially-extending segment.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIGS. 6A-6C are side views of a variety of support arm configurations in accordance with additional embodiments of the present technology.

DETAILED DESCRIPTION OF THE INVENTION

Specific embodiments of the present technology are now described with reference to the figures, wherein like reference numbers indicate identical or functionally similar elements. The terms "distal" and "proximal" are used in the following description with respect to a position or direction relative to the treating clinician or with respect to a prosthetic heart valve device. For example, "distal" or "distally" are a position distant from or in a direction away from the clinician when referring to delivery procedures or along a vasculature. Likewise, "proximal" and "proximally" are a position near or in a direction toward the clinician. With respect to a prosthetic heart valve device, the terms "proximal" and "distal" can refer to the location of portions of the device with respect to the direction of blood flow. For example, proximal can refer to an upstream position or a position of blood inflow, and distal can refer to a downstream position or a position of blood outflow.

The following detailed description is merely exemplary in nature and is not intended to limit the present technology or the application and uses of the present technology. Although the description of embodiments hereof are in the context of treatment of heart valves and particularly a mitral valve, the present technology may also be used in any other body passageways where it is deemed useful. Furthermore, there is no intention to be bound by any expressed or implied theory presented in the preceding technical field, background, brief summary or the following detailed description.

Embodiments of the present technology as described herein can be combined in many ways to treat one or more of many valves of the body including valves of the heart such as the mitral valve. The embodiments of the present technology can be therapeutically combined with many known surgeries and procedures, for example, such embodiments can be combined with known methods of accessing the valves of the heart such as the mitral valve with antegrade or retrograde approaches, and combinations thereof.

Figure 1:
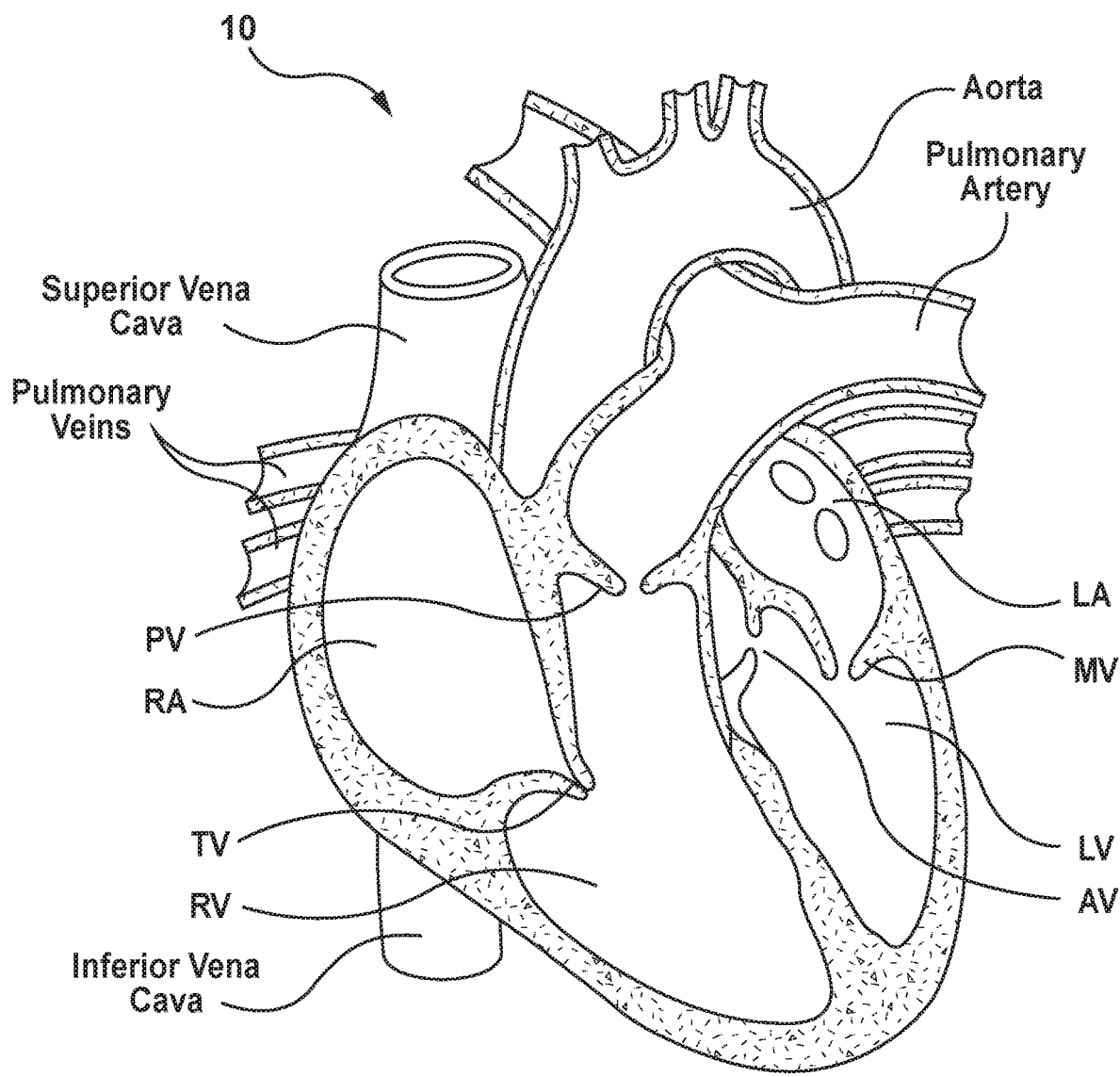
FIG. 1 is a schematic sectional illustration of a mammalian heart having native valve structures.
Figure 2A:
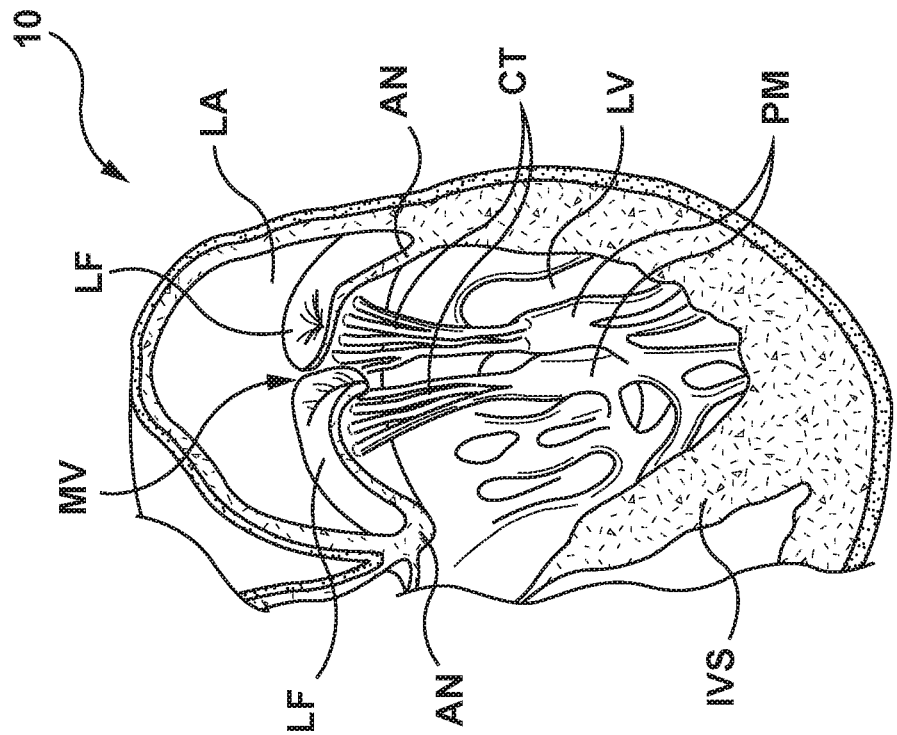
FIG. 2A is a schematic sectional illustration of a left ventricle of a mammalian heart showing anatomical structures and a native mitral valve.

FIG. 1 is a schematic sectional illustration of a mammalian heart 10 that depicts the four heart chambers (right atria RA, right ventricle RV, left atria LA, left ventricle LV) and native valve structures (tricuspid valve TV, mitral valve MV, pulmonary valve PV, aortic valve AV). FIG. 2A is a schematic sectional illustration of a left ventricle LV of a mammalian heart 10 showing anatomical structures and a native mitral valve MV. Referring to FIGS. 1 and 2A together, the heart 10 comprises the left atrium LA that receives oxygenated blood from the lungs via the pulmonary veins. The left atrium LA pumps the oxygenated blood through the mitral valve MV and into the left ventricle LV during ventricular diastole. The left ventricle LV contracts during systole and blood flows outwardly through the aortic valve AV, into the aorta and to the remainder of the body.

Figure 2B:
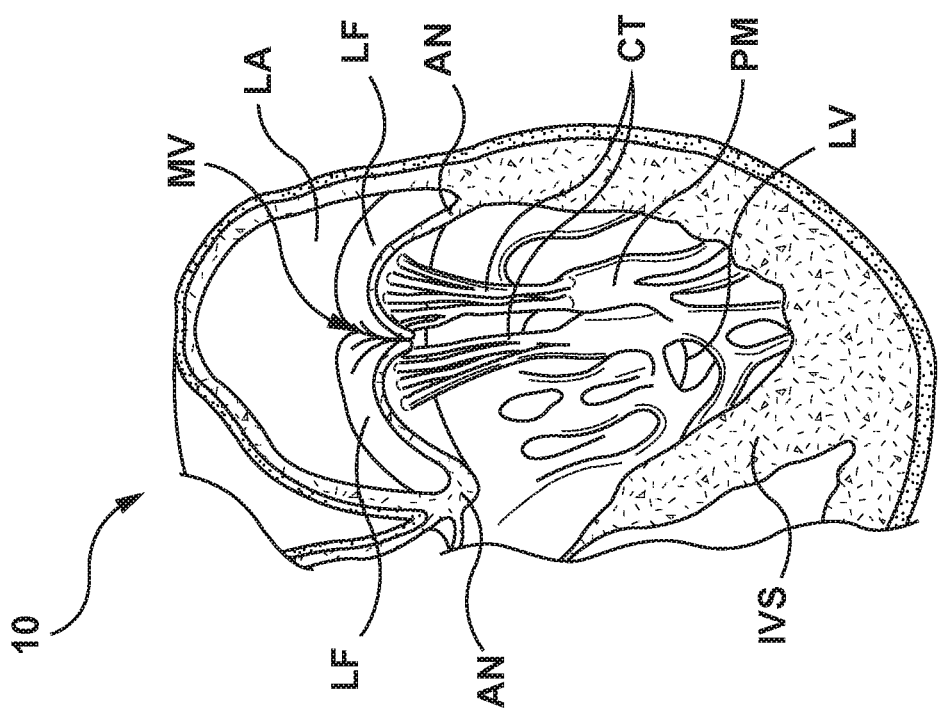
FIG. 2B is a schematic sectional illustration of the left ventricle of a heart having a prolapsed mitral valve in which the leaflets do not sufficiently coapt and which is suitable for replacement with various embodiments of prosthetic heart valves in accordance with the present technology.

In a healthy heart, the leaflets LF of the mitral valve MV meet evenly at the free edges or "coapt" to close and prevent back flow of blood during contraction of the left ventricle LV (FIG. 2A). Referring to FIG. 2A, the leaflets LF attach the surrounding heart structure via a fibrous ring of connective tissue called an annulus AN. The flexible leaflet tissue of the mitral leaflets LF are connected to papillary muscles PM, which extend upwardly from the lower wall of the left ventricle LV and the interventricular septum IVS, via branching tendons called chordae tendinae CT. In a heart 10 having a prolapsed mitral valve MV in which the leaflets LF do not sufficiently coapt or meet, as shown in FIG. 2B, leakage from the left ventricle LV into the left atrium LA will occur. Several structural defects can cause the mitral leaflets LF to prolapse and regurgitation to occur, including ruptured chordae tendinae CT, impairment of papillary muscles PM (e.g., due to ischemic heart disease), and enlargement of the heart and/or mitral valve annulus AN (e.g., cardiomyopathy).

Figure 3:
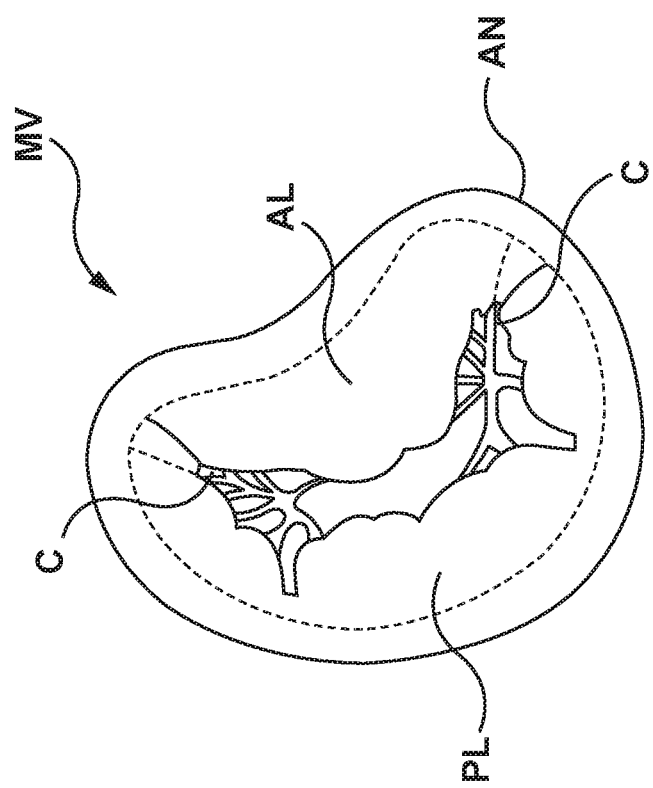
FIG. 3 is a schematic illustration of a superior view a mitral valve isolated from the surrounding heart structures and showing the annulus and native leaflets.

FIG. 3 is a superior view of a mitral valve MV isolated from the surrounding heart structures and further illustrating the shape and relative sizes of the leaflets LF and annulus AN. As shown, the mitral valve MV generally has a "D" or kidney shape. The mitral valve MV includes an anterior leaflet AL which meets a posterior leaflet PL at a coaptation line when closed. When the anterior leaflet AL and posterior leaflet PL fail to meet, regurgitation between the leaflets AL, PL or at commissures C at the corners between the leaflets can occur.

Embodiments of prosthetic heart valve devices and associated methods in accordance with the present technology are described in this section with reference to FIGS. 4A-10. It will be appreciated that specific elements, substructures, uses, advantages, and/or other aspects of the embodiments described herein and with reference to FIGS. 4A-10 can be suitably interchanged, substituted or otherwise configured with one another in accordance with additional embodiments of the present technology.

Provided herein are systems, devices and methods suitable for percutaneous delivery and implantation of prosthetic heart valves in a heart of a patient. In some embodiments, methods and devices are presented for the treatment of valve disease by minimally invasive implantation of artificial or prosthetic heart valves. For example, a prosthetic heart valve device, in accordance with embodiments described herein, can be implanted for replacement of a diseased or damaged native mitral valve or prior implanted prosthetic mitral valve in a patient, such as in a patient suffering from a prolapsed mitral valve illustrated in FIG. 2A. In further embodiments, the device is suitable for implantation and replacement of other diseased or damaged heart valves or prior implanted prosthetic heart valves, such as tricuspid, pulmonary and aortic heart valves.

Figure 4A:
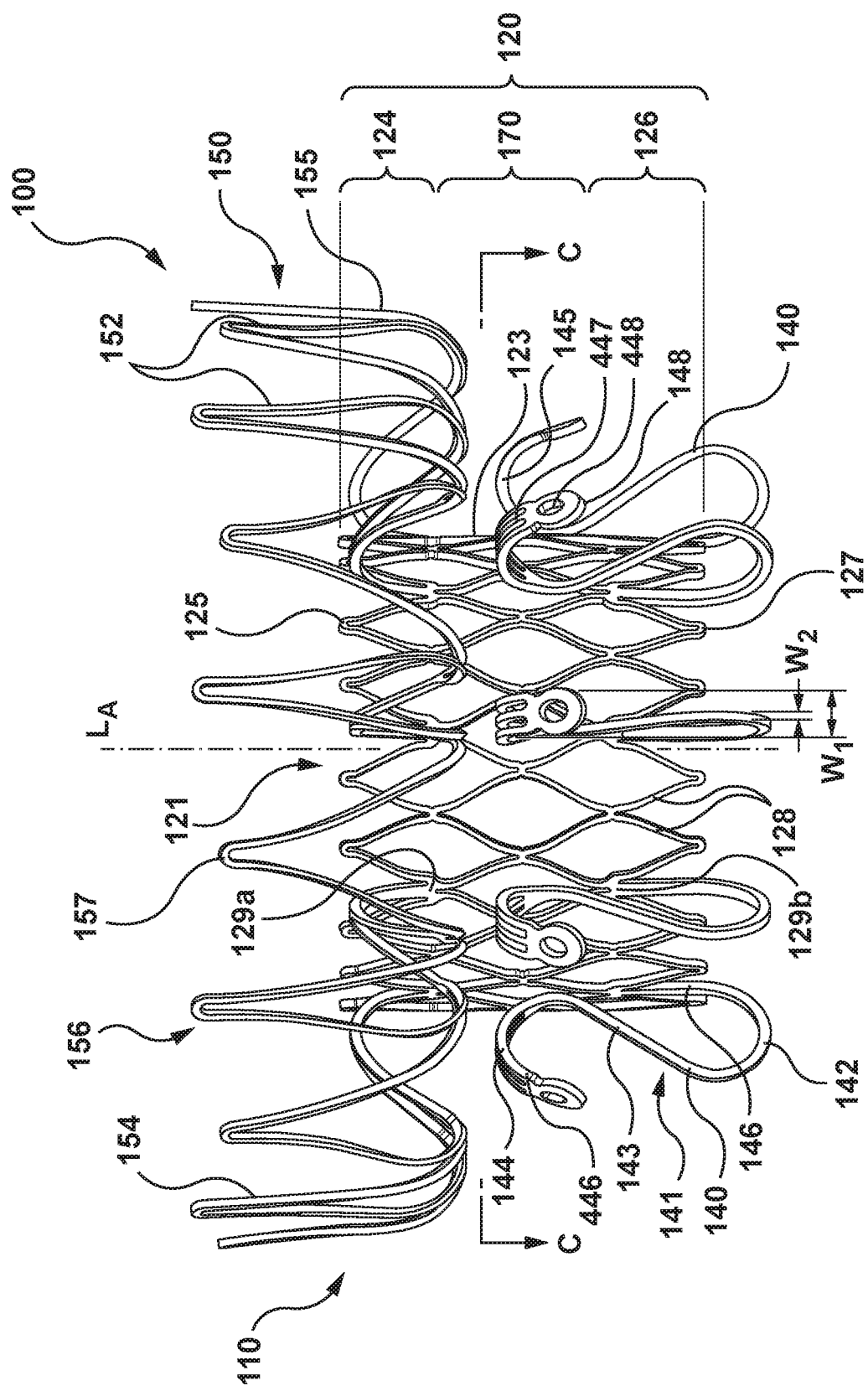
FIG. 4A is a side view of a heart valve prosthesis in a deployed or expanded configuration (e.g., a deployed state) in accordance with an embodiment of the present technology.
Figure 4B:
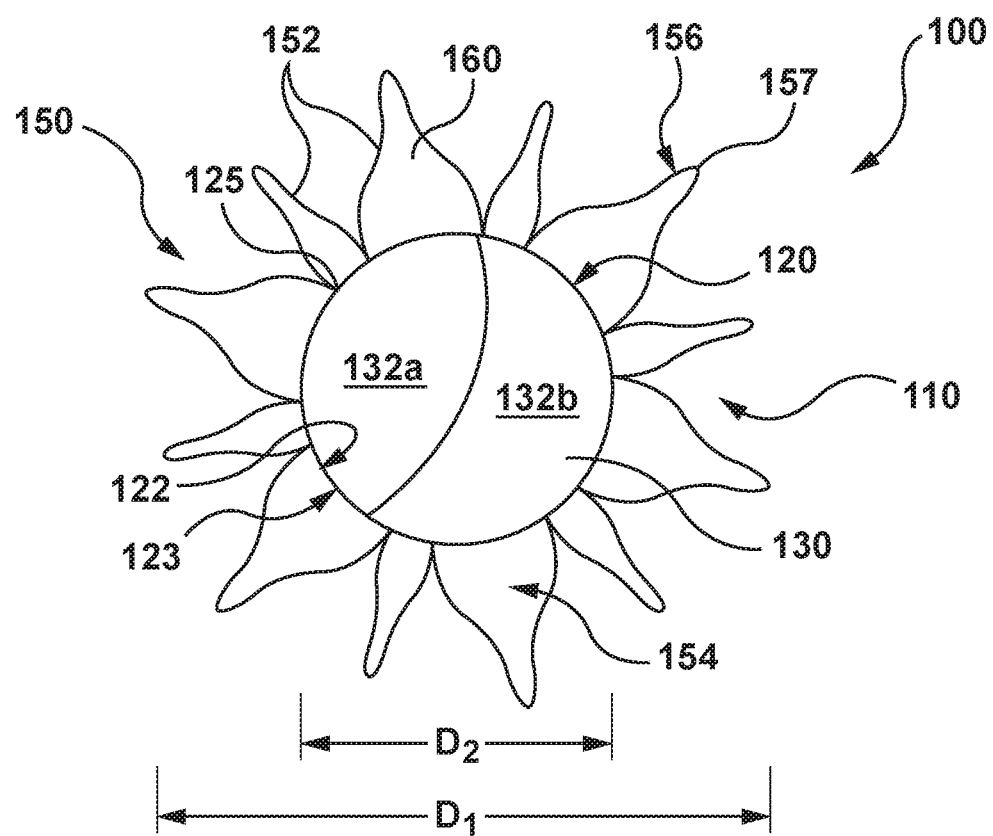
FIG. 4B is a top view of the heart valve prosthesis of FIG. 4A in accordance with an embodiment of the present technology.
Figure 4C:
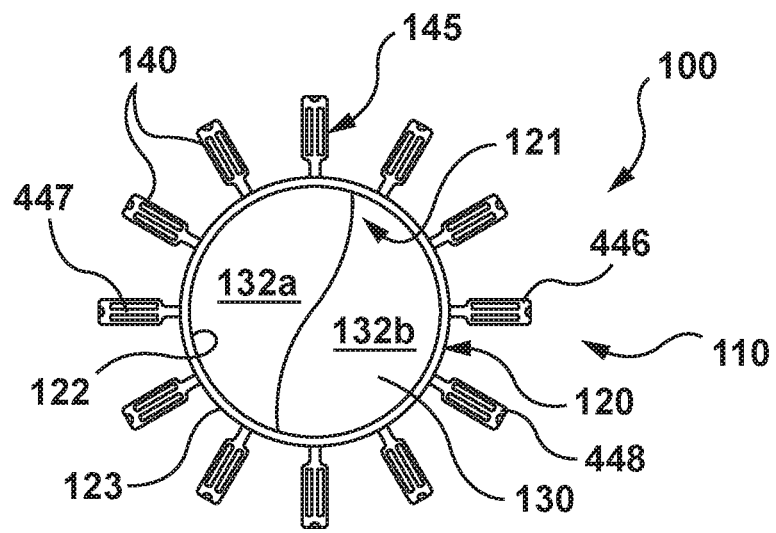
FIG. 4C is a top view of the heart valve prosthesis taken along lines 4C-4C of FIG. 4A and in accordance with an embodiment of the present technology.

FIG. 4A is a side view of a heart valve prosthesis or a prosthetic heart valve device 100 in a radially expanded or deployed configuration (e.g., a deployed state) in accordance with an embodiment of the present technology. FIG. 4B is a top view of the heart valve prosthesis 100 as configured in FIG. 4A, and FIG. 4C is a top view of the prosthesis 100 taken along lines C-C of FIG. 4A. Referring to FIGS. 4A-4C together, the heart valve prosthesis 100 includes a frame or stent-like support structure 110 that includes a tubular portion or structural valve support 120 that defines a lumen 121 for retaining, holding and/or securing a prosthetic valve component 130 therein. The valve support 120 can be generally cylindrical in shape having an upstream portion 124 at a first end 125 and a downstream portion 126 at a second end 127 that are oriented along a longitudinal axis LA of the valve support 120 (FIG. 4A). The frame 110 further includes one or more support arms 140 extending radially outward from the valve support 120 and generally in an upstream direction from the downstream portion 126 of the valve support 120 (e.g., to reach behind native leaflets of the mitral valve and engage cardiac tissue in the subannular region within the left ventricle). At least some of the support arms 140 can have a curvilinear shape 141 configured to atraumatically engage the native annulus and substantially absorb distorting forces such that the prosthesis 100 is supported by the annulus when prosthetic valve component 130 is closed during systole.

In some embodiments, and as shown in the radially expanded configuration of FIG. 4A, the frame 110 further includes a radially-extending segment or radial extension portion 150 at least partially surrounding and extending from the upstream portion 124 of the valve support 120. The radially-extending segment 150 can include a plurality of self-expanding struts 152 configured to radially expand when the prosthesis 100 is deployed to the expanded configuration. In some arrangements, the radially-extending segment 150 can engage tissue on or above the annulus when implanted within a native mitral valve space. In this embodiment, the radially-extending segment 150 can retain the valve support 120 in a desired position within the native valve region (e.g., between the native leaflets and annulus of the mitral valve). Referring to FIG. 4B, the radially-extending segment 150 and/or the valve support 120 can include a sealing material 160 that can extend around an upper or upstream surface 154 or a lower or downstream surface 155 (FIG. 4A) of the radially-extending segment 150, and/or around an interior wall 122 or an exterior wall 123 of the valve support 120 to prevent leakage of blood (e.g., paravalvular leakage) between the implanted prosthesis 100 and the native heart tissue.

Referring to FIG. 4B, the radially-extending segment 150 and valve support 120 are shown having generally circular cross-sectional shapes with the radially-extending segment 150 having a cross-sectional dimension $D_1$ that is greater than a cross-sectional dimension $D_2$ of the valve support 120. In some embodiments, the radially-extending segment 150, the valve support 120 or both can have other cross-sectional shapes, such as to accommodate the D-shaped or kidney-shaped mitral valve. For example, the radially-extending segment 150 and/or valve support 120 may expand to an irregular, non-cylindrical, or oval-shaped configuration for accommodating the mitral valve or other valves. Furthermore, the native valves (e.g., mitral, aortic) can be uniquely sized and/or have other unique anatomical shapes and features that vary between patients, and the prosthesis 100 for replacing or repairing such valves can be suitable for adapting to the size, geometry and other anatomical features of such native valves. For example, the radially-extending segment 150 can expand within the native heart valve region while simultaneously being flexible so as to conform to the region engaged by the radially-extending segment 150.

FIGS. 4A and 4B show the radially-extending segment 150 having the plurality of struts 152 that outwardly extend from the exterior wall 123 at the first end 125 of the valve support 120. In one embodiment, the struts 152 are arranged relatively evenly about a circumference of the valve support 120, and individual struts 152 join an adjacent strut 152 at a crown 156. In one embodiment the crowns 156 have an atraumatic tip 157 that prevents injury to the cardiac tissue during deployment and through the cardiac cycle. Examples of suitable radially-extending segments 150 are described in U.S. Patent Publication No. 2015/0119982, which is incorporated herein by reference in its entirety.

Referring back to FIGS. 4A and 4C, a plurality of support arms 140 extend from the downstream portion 126 of the valve support 120, and are generally evenly spaced about the circumference of the exterior wall 123 of the valve support 120 (FIG. 4C). In alternative arrangements, not shown, the support arms 140 can be unevenly spaced, grouped, irregularly spaced, etc. about the circumference. In a particular example, the support arms 140 can be grouped closer together and extend from the valve support 120 at positions that generally align with the anterior and posterior leaflets of the mitral valve when deployed. The embodiment shown in FIG. 4C has twelve support arms 140 evenly spaced about the circumference of the valve support 120. In alternative arrangements, the prosthesis 100 can include less than 12 support arms 140, e.g., two support arms, two to six support arms, greater than six support arms, nine support arms, etc., or more than twelve support arms 140.

Referring to FIG. 4A, the support arms 140 may extend from the valve support 120 at or near the second end 127 and may be described as extending generally toward the upstream portion 124 along or in parallel with the exterior wall 123 of the valve support 120. As shown, the support arm 140 can have the generally curvilinear shape 141 or similar geometry. The curvilinear shape 141 includes opposing arcuate or curved regions 142, 144 longitudinally separated by a slanted elongate or straight region 143 that extends therebetween. When positioned for use within a native mitral valve, arcuate region 142 of a curvilinear support arm 140 may be referred to as a downstream curved segment 142 and arcuate region 144 of the curvilinear support arm 140 may be referred to as an upstream curved segment 144.

In some embodiments, the curvilinear shape 141 includes a first arcuate (e.g., curved) region 142 formed to curve in a direction toward the exterior wall 123 to engage a portion of at least one leaflet of the native heart valve or other structures in the heart valve region, such as chordae tendinae. In one embodiment, the first arcuate region 142 may extend around a downstream edge of the native valve leaflet. In a medial section of the support arm 140, the support arm includes the straight region 143 configured to follow from the first arcuate region 142 and to slant in a direction toward the exterior wall 123 at an intermediate or middle portion 170 of the valve support 120. In a free-end section of the support arm 140 proximate the first end 125 of the valve support 120, and following the straight or elongate region 143 along the curvilinear shape 141, the support arm 140 further includes a second arcuate (e.g., curved) region 144 formed to curve in a direction away from the exterior wall 123 of the valve support 120 and to engage tissue at or proximate to the native heart valve when implanted. In a particular example, the second arcuate region 144 can engage subannular tissue and/or portions of a heart chamber wall, e.g., a ventricular wall, in an atraumatic matter. In reference to FIG. 4A, and in a particular embodiment, the first arcuate region 142 is longitudinally separated from the second arcuate region 144 by the straight or elongate region 143 to form or define a substantially S-shaped profile.

In the embodiment shown in FIGS. 4A and 4C, the second arcuate region 144 on each of the support arms 140 provides or defines a contact area or landing zone 145 that is configured to atraumatically engage tissue at or near the subannular tissue so as to inhibit tissue erosion and/or resist movement of the prosthesis 100 in an upstream direction during ventricular systole, as is described further herein. As illustrated, the second arcuate region 144 includes a widened and/or flattened portion 446 that forms the landing zone 145. As shown in FIG. 4A, the widened portion 446 has a first width $W_1$ that is greater than a width $W_2$ at the first arcuate region 142 of the support arm 140. When the prosthesis 100 is deployed and in contact with tissue (e.g., subannular tissue, native leaflets, ventricle wall, etc.) via the widened portion 446, the landing zone 145 effectively distributes native tissue contact over a greater surface area to inhibit tissue erosion and to distribute load stress on the support arms 140. In the embodiment shown in FIGS. 4A and 4C, the landing zone 145 includes grooves 447 formed along the widened portion 446 that can provide additional barriers against movement of the landing zone 145 with respect to the contacted tissue. In alternative arrangements, the landing zone 145 can include raised portions, bumps, cut-outs and other features that provide additional movement resistance against the contacted tissue once deployed. In various arrangements, by resisting movement of the landing zone 145 against the contacted native tissue, the support arms 140 provide atraumatic contact in a manner that limits or inhibits tissue erosion and/or abrasion following implantation of the prosthesis 100. In certain embodiments, and as shown in FIGS. 4A and 4C, the support arm 140 includes an arm tip 148 that can be rounded or otherwise atraumatic to cardiac tissue engaged by the arm tip 148 either during deployment or when fully implanted. In the illustrated embodiment, the arm tip 148 includes a hole 448 for attaching the support arms 140 to a delivery catheter (not shown) in a radially-compressed configuration for delivery to a target site. Additionally, or alternatively, one or more of the holes 448 may be filled with a secondary material (e.g. Tantalum, Platinum, Gold) for improved visibility during fluoroscopy-guided delivery. In alternative arrangements, the support arms 140 may not include a hole 448 and/or other landing zone features (e.g., grooves 447) without departing from the scope hereof.

In some embodiments described herein, and in order to transform or self-expand between an initial compressed configuration (e.g., in a delivery state, not shown) and the deployed configuration (FIG. 4A), the frame 110 is formed from a resilient or shape memory material, such as a nickel titanium alloy (e.g., nitinol), that has a mechanical memory to return to the deployed or expanded configuration. In one embodiment, the frame 110 can be a unitary structure that defines the radially-extending segment 150 at the inflow portion of the prosthesis 100, the valve support 120 and the plurality of support arms 140, and the frame 110 so described may be made from stainless steel, a pseudo-elastic metal such as nickel titanium alloy or nitinol, or a so-called super alloy, which may have a base metal of nickel, cobalt, chromium, or other metal. In some arrangements, the frame 110 can be formed as a unitary structure, for e.g., from a laser cut, fenestrated, nitinol or other metal tube. Mechanical memory may be imparted to the structure that forms the frame 110 by thermal treatment to achieve a spring temper in the stainless steel, for example, or to set a shape memory in a susceptible metal alloy, such as nitinol. The frame 110 may also include polymers or combinations of metals, polymers or other materials.

In one embodiment, the frame 110 can be a flexible metal frame or support structure having a plurality of ribs and/or struts (e.g., struts 128, 152) geometrically arranged to provide a latticework capable of being radially compressed (e.g., in a delivery state, not shown) for delivery to a target native valve site, and capable of radially expanding (e.g., to the radially expanded configuration shown in FIG. 4A) for deployment and implantation at the target native valve site. Referring to the valve support 120 shown in FIG. 4A, the ribs and struts 128 can be arranged in a plurality of geometrical patterns that can expand or flex and contract while providing sufficient resilience and strength for maintaining the integrity of the prosthetic valve component 130 housed within. For example, the struts 128 can be arranged in a circumferential pattern about the longitudinal axis $L_A$, wherein the circumferential pattern includes a series of diamond, zig-zagged, sinusoidal, or other geometric shapes.

In other embodiments, the frame 110 can include separately manufactured components that are coupled, linked, welded, or otherwise mechanically attached to one another to form the frame 110. For example, the radially-extending segment 150 can be coupled to the upstream portion 124 of the valve support 120 (e.g., at attachments points 129a on the struts 128 as defined by a diamond-shaped geometry of the valve support 120). Likewise, the support arms 140 can be coupled to the downstream portion 126 of the valve support 120 (e.g., at attachment points 129b on the struts 128 as defined by the diamond-shaped geometry of the valve support 120). Other arrangements and attachment points are contemplated for coupling one or more of the support arms 140 and radially-extending segment 150 to the valve support 120. In particular embodiments, and as shown in FIG. 4A, the support arms 140 can be coupled to the valve support 120 via an arm post 146. In one embodiment, the arm post 146 can be integral with the frame 110 such that the arm post 146 is an extension of one or more struts 128. In another embodiment, the arm posts 146 and valve support 120 may be coupled by a variety of methods known in the art, e.g., soldering, welding, bonding, rivets or other fasteners, mechanical interlocking, or any combination thereof. In one embodiment, the valve support 120 can be a balloon-expandable tubular metal stent, and the radially-extending segment 150 and the support arms 140 of the frame 110 may be formed from material and by methods so as to be self-expanding as described above. In another embodiment in accordance herewith, support arms 140 may extend from or be coupled to an intermediate or middle portion 170 of the valve support 120 without departing from the scope hereof.

Referring to FIGS. 4B-4C, the prosthetic valve component 130 may be coupled to the interior wall 122 of the valve support 120 for governing blood flow through the heart valve prosthesis 100. For example, the prosthetic valve component 130 can include a plurality of leaflets 132 (shown individually as 132a-b) that coapt and are configured to allow blood flow through the prosthesis 100 in a downstream direction (e.g., from the first end 125 to the second end 127) and inhibit blood flow in an upstream direction (e.g., from the second end 127 to the first end 125). While the prosthetic valve component 130 is shown having a bicuspid arrangement, it is understood that the prosthetic valve component 130 can have three leaflets 132 (tricuspid arrangement, not shown) or more than three leaflets 132 that coapt to close the prosthetic valve component 130. In one embodiment, the leaflets 132 can be formed of bovine pericardium or other natural material (e.g., obtained from heart valves, aortic roots, aortic walls, aortic leaflets, pericardial tissue, such as pericardial patches, bypass grafts, blood vessels, intestinal submucosal tissue, umbilical tissue and the like from humans or animals) that are mounted to the interior wall 122 of the valve support 120. In another embodiment, synthetic materials suitable for use as valve leaflets 132 include DACRON® polyester (commercially available from Invista North America S.A.R.L. of Wilmington, Del.), other cloth materials, nylon blends, polymeric materials, and vacuum deposition nitinol fabricated materials. In yet a further embodiment, valve leaflets 132 can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It can be further desirable that the leaflet material is durable and not subject to stretching, deforming, or fatigue.

Figure 5A:
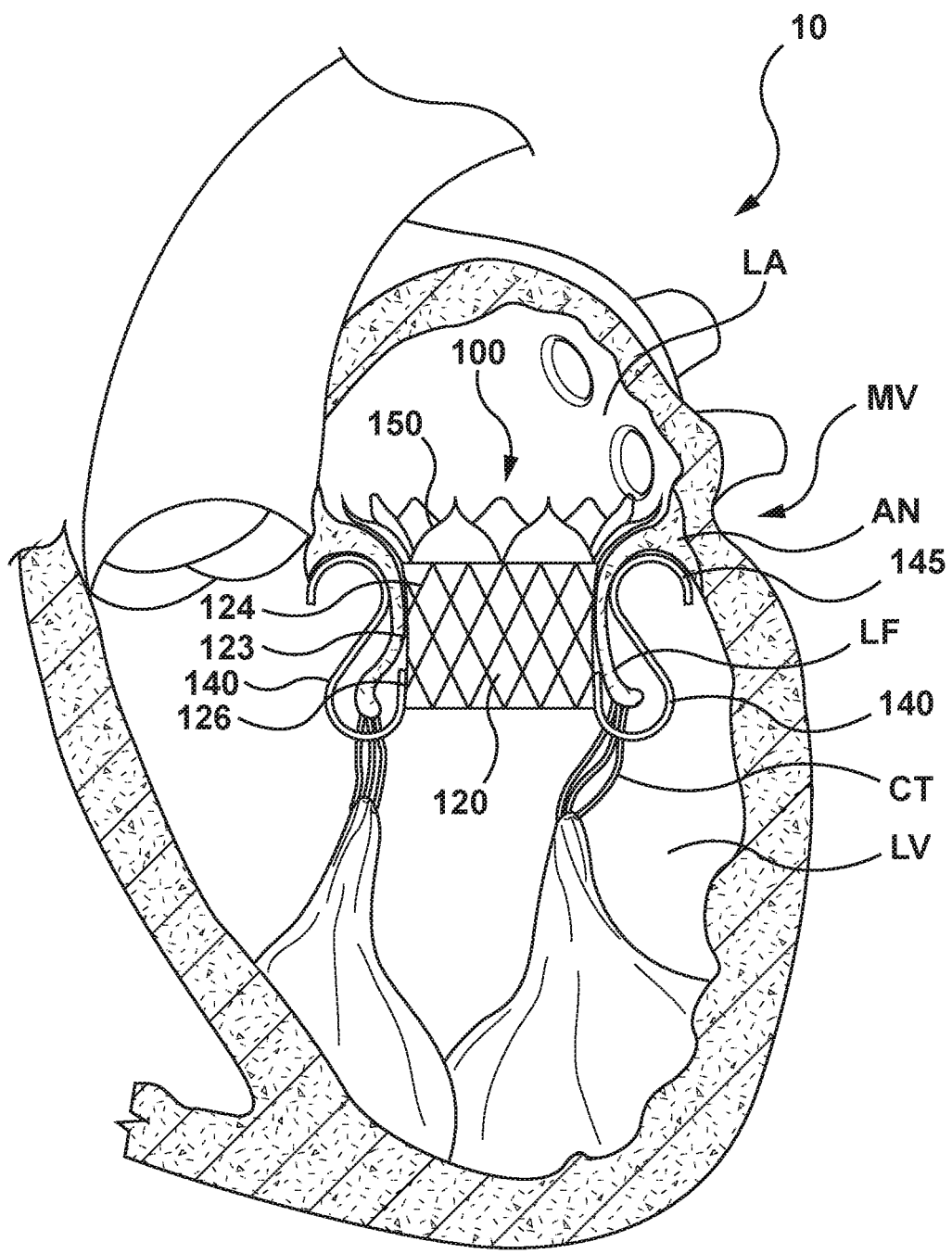
FIG. 5A illustrates a cut-away view of a heart showing a partial side view of a heart valve prosthesis implanted at a native mitral valve in accordance with an embodiment of the present technology.

FIG. 5A is a schematic illustration showing a partial side view the prosthesis 100 implanted at a native mitral valve region of the heart 10 in accordance with an embodiment of the present technology. The prosthesis 100 is shown in FIG. 5A having only two support arms 140 for purposes of illustration only. It is understood that the prosthesis 100, in some arrangements, can have more than two support arms 140, e.g., greater than six support arms, etc. Generally, when implanted, the upstream portion 124 of the valve support 120 is oriented to receive blood inflow from a first heart chamber, e.g., left atrium LA for mitral valve MV replacement, left ventricle for aortic valve replacement, etc., and the downstream portion 126 is oriented to release blood outflow into a second heart chamber or structure, e.g., left ventricle LV for mitral valve MV replacement, aorta for aortic valve replacement.

In operation, the heart valve prosthesis 100 can be intravascularly delivered to a desired native valve region of the heart 10, such as near the mitral valve MV, while in the radially compressed configuration (not shown) and within a delivery catheter (not shown). Referring to FIG. 5A, the prosthesis 100 can be advanced to a position within or downstream of the native mitral valve annulus AN where the support arms 140 and the downstream portion 126 of the valve support 120 are released from the delivery catheter. The delivery catheter can then release the upstream portion 124 of the valve support 120 and the radially-extending segment 150 at a position within or upstream of the native mitral valve MV so as to enlarge toward the radially expanded configuration and engage the native tissue within the native heart valve region. Once released from the delivery catheter, the prosthesis 100 can be positioned such that the radially-extending segment 150 resides within the left atrium and engages tissue at or near the supra-annular region. The prosthesis 100 is further positioned such that the support arms 140 engage outward-facing surfaces of the native leaflets LF to capture the leaflets between the support arms 140 and the exterior wall 123 of the valve support 120. The contact area or landing zone 145 of each of the support arms 140 is configured to engage tissue at or near the subannular tissue so as to resist movement of the prosthesis 100 in an upstream direction during ventricular systole, as is described further herein.

Figure 5B:
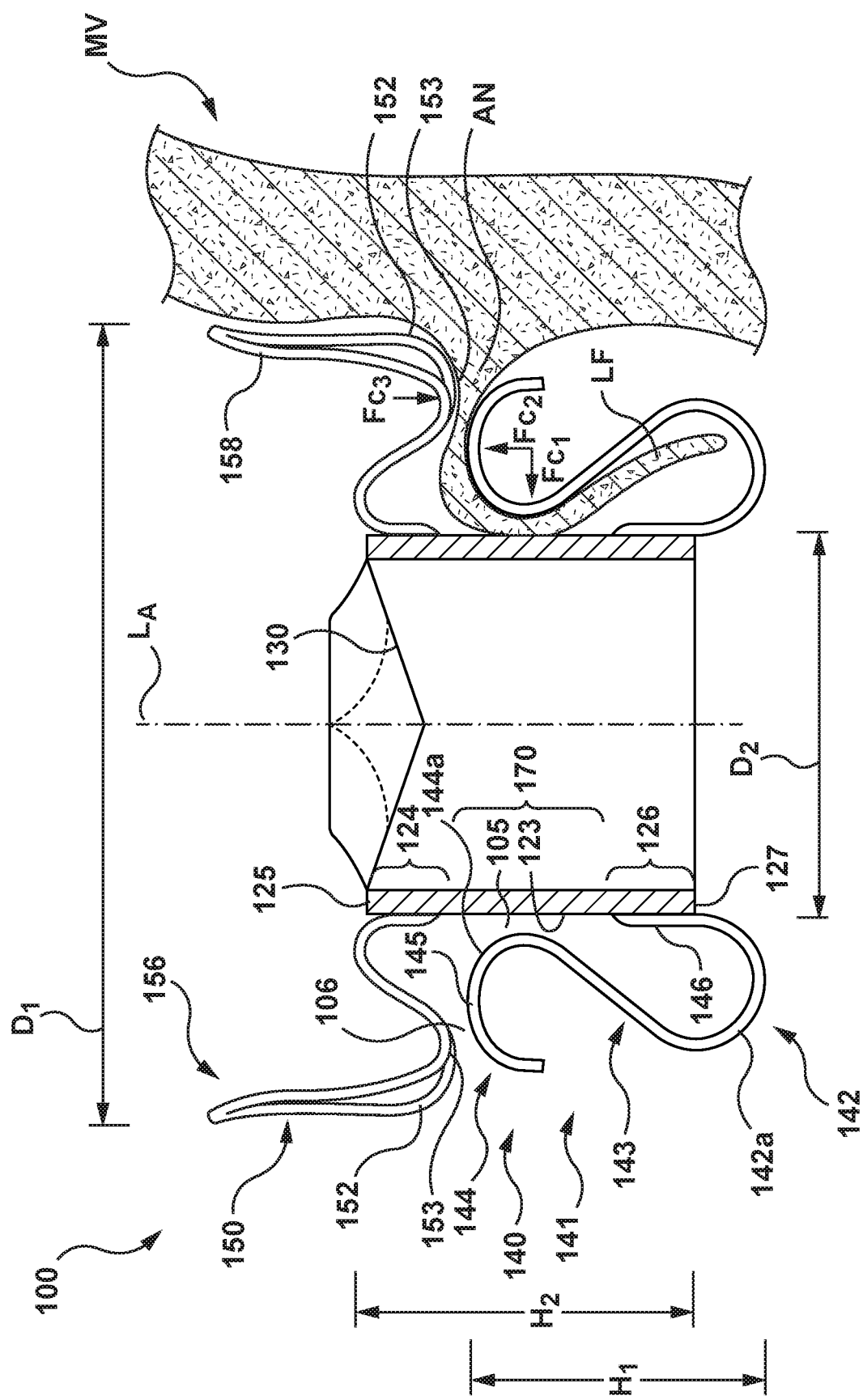
FIG. 5B is an enlarged sectional view of the heart valve prosthesis of FIG. 5A shown in a deployed configuration (e.g., expanded state) in accordance with an embodiment of the present technology.

FIG. 5B is an enlarged sectional view of the heart valve prosthesis 100 of FIG. 5A shown in a radially expanded configuration (e.g., a deployed state) and in accordance with an embodiment of the present technology. In FIG. 5B, the prosthesis 100 is schematically shown positioned at a mitral valve MV on the right-hand side of the illustration. When deployed and implanted, the heart valve prosthesis 100 is configured to position the prosthetic valve component 130, which is retained or held within the valve support 120, in a desired location and orientation within the native mitral valve MV. Referring to FIGS. 5A and 5B together, several features of the prosthesis 100 provide resistance to movement of the prosthesis 100, promote tissue ingrowth, minimize or prevent paravalvular leakage and/or minimize native tissue erosion when implanted in the radially expanded configuration. For example, the radially-extending segment 150 can be positioned to expand within the atrial space above the mitral valve and engage cardiac tissue within the atrial space. In particular, at least a lower surface or apex 153 of an arching or S-shaped strut 152 can provide a tissue engaging region for contacting the supra-annular tissue, for example to provide sealing against paravalvular leakage and to inhibit downstream migration of the prosthesis 100 relative to the native annulus.

In some embodiments, an upward oriented lip portion 158 of the struts 152 that rise to form the crowns 156 can provide further tissue contact zones that can further inhibit downstream movement of the prosthesis 100 relative to the native annulus, and inhibit rocking or side-to-side rotation of the prosthesis 100 within the native valve during the cardiac cycle, thereby inhibiting paravalvular leakage and assuring alignment of the prosthetic valve component 130 within the native annulus. In other embodiments, the radially-extending segment 150 can be a flange, a brim, a ring, finger-like projections or other projection into the atrial space for at least partially engaging tissue at or above a supra-annular region thereof.

Referring to FIGS. 5A and 5B together, the support arms 140 are shown having the curvilinear shape 141 and extending from the downstream portion 126 of the valve support 120. The support arms 140 are configured to engage both the native leaflets (if present) and/or the subannular region of the mitral valve MV within the ventricular space. In one embodiment, the support arms 140 are configured to engage an outside surface (e.g., ventricle-facing side) of the leaflet such that the native leaflet is captured between the support arm 140 and the exterior wall 123 of the valve support 120. In one such embodiment, the preformed curvilinear shape 141 of the support arm 140, for example at a transitional apex 144a of the second arcuate region 144, can be biased toward the exterior wall 123 of the valve support 120 such that a compressive force $Fc_1$ presses the leaflet LF against the exterior wall 123 in a manner that pinches, grasps, crimps or otherwise confines the leaflet within the space 105 between the support arm 140 and the exterior wall 123 of the valve support 120.

Figure 5C:
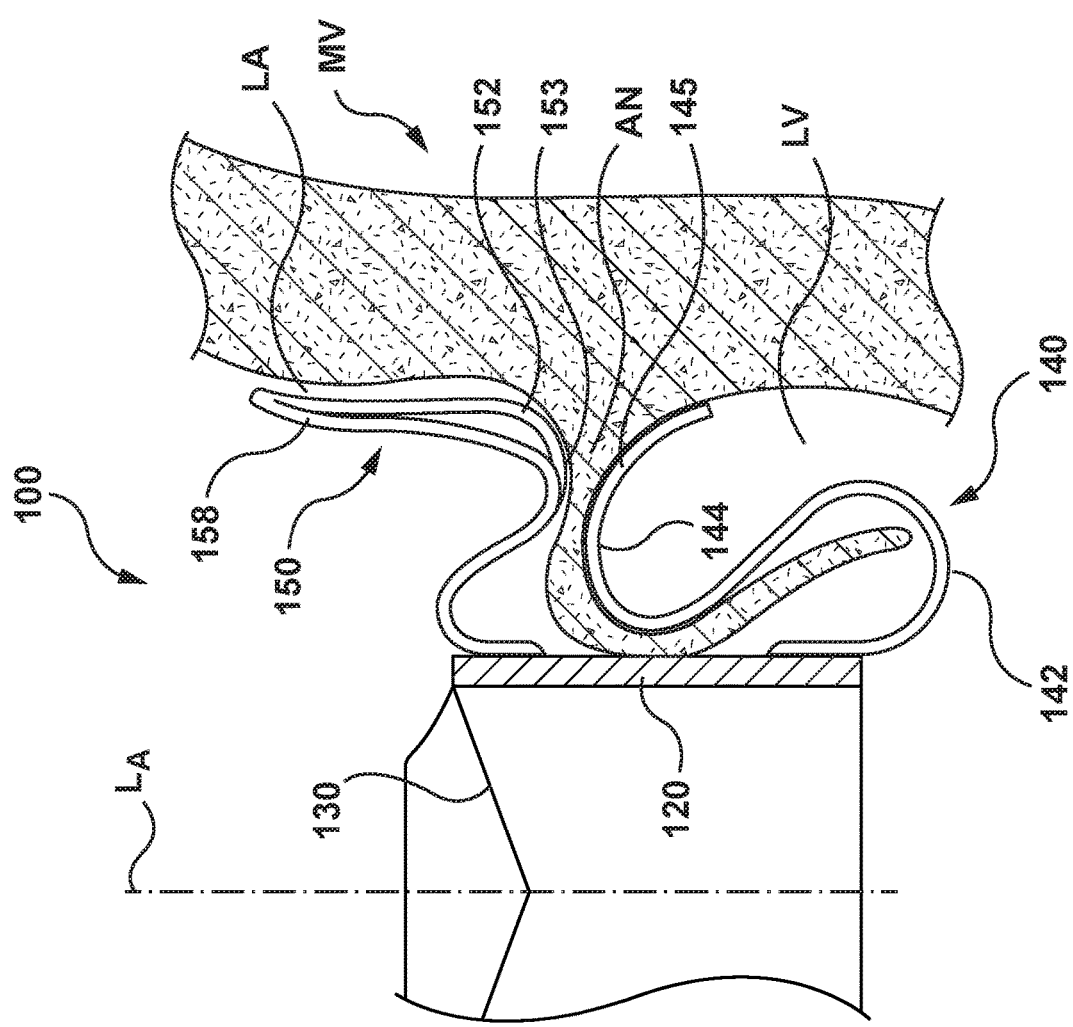
FIG. 5C is an enlarged sectional view of a portion of a heart valve prosthesis shown in a deployed configuration (e.g., expanded state) in accordance with another embodiment of the present technology.

To further inhibit upstream migration of the prosthesis 100 with respect to the native valve annulus AN, the second arcuate region 144 is configured to engage the subannular region (e.g., behind the leaflet LF) via the contact area or landing zone 145. In an additional embodiment, the second arcuate region 144 can contact tissues below the annulus AN, such as the ventricle wall (as shown in FIG. 5C). By contacting the subannular region (FIGS. 5A and 5B) and/or the tissues below the annulus AN (FIG. 5C) via, for example, the widened portion 446 (FIGS. 4A and 4C) that extends to arm tip 148, the landing zone 145 distributes surface contact over a larger region to inhibit tissue erosion and to distribute load stress on the support arms 140 in an atraumatic manner.

In various arrangements, the curvilinear shape 141 of the support arm 140 can form a substantially S-shaped profile. In certain arrangements, the support arms 140 can be more flexible (e.g., than other portions of the frame 110) and/or be made of resilient material (e.g., shape-memory material, super-elastic material, etc.) that can absorb forces exerted on the support arms 140 when implanted in the heart 10 and during the cardiac cycle. For example, these forces can cause the substantially S-shaped profile to temporarily deform, deflect or otherwise change shape. Likewise, the curvilinear shape 141 of the support arms can provide compressive forces $Fc_2$ in an upstream direction (e.g., at the contact zone 145) and against annulus tissue. In one embodiment, the apex 153 (e.g., lower surface) of the radially-extending segment 150 can be longitudinally separated from the landing zone 145 of the second arcuate region by a gap 106. When implanted, the gap 106 can be sized to receive annular tissue therein. In one embodiment, the apex 153 of the arching strut 152 can provide a downward compressive force $Fc_3$ on the contacted tissue of the annulus that opposes the compressive force $F_{C2}$ across the gap 106. Accordingly, the compressive forces $Fc_2$ and $Fc_3$ may be aligned and/or opposed to each other such that annular tissue is captured between the radially-extending segment 150 and the support arms 140 having the preformed curvilinear shape 141. In some embodiments, the struts 152 can be circumferentially- and radially-aligned with the second arcuate region 144 of the support arms 140 such that the compressive force $Fc_1$ is directly opposed to the compressive force $Fc_3$ (shown in FIG. 5B) to effectively pinch the annulus AN therebetween.

In some embodiments, the portions of the prosthesis 100, such as the radially-extending segment 150, the valve support 120 and/or the support arms 140 can be provided with a sealing material 160 (FIG. 4B) to cover at least portions of the prosthesis 100. The sealing material 160 can prevent paravalvular leakage as well as provide a medium for tissue ingrowth following implantation, which can further provide biomechanical retention of the prosthesis 100 in the desired deployment location within the native heart valve region. In some embodiments, the sealing material 160 or portions thereof may be a low-porosity woven fabric, such as polyester, DACRON® polyester, or polytetrafluoroethylene (PTFE), which creates a one-way fluid passage when attached to the frame 110. In one embodiment, the sealing material 160 or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for at least portions of the sealing material 160, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the sealing material 160 or portions thereof may be a natural graft material, such as pericardium or another membranous tissue.

Figure 6A:
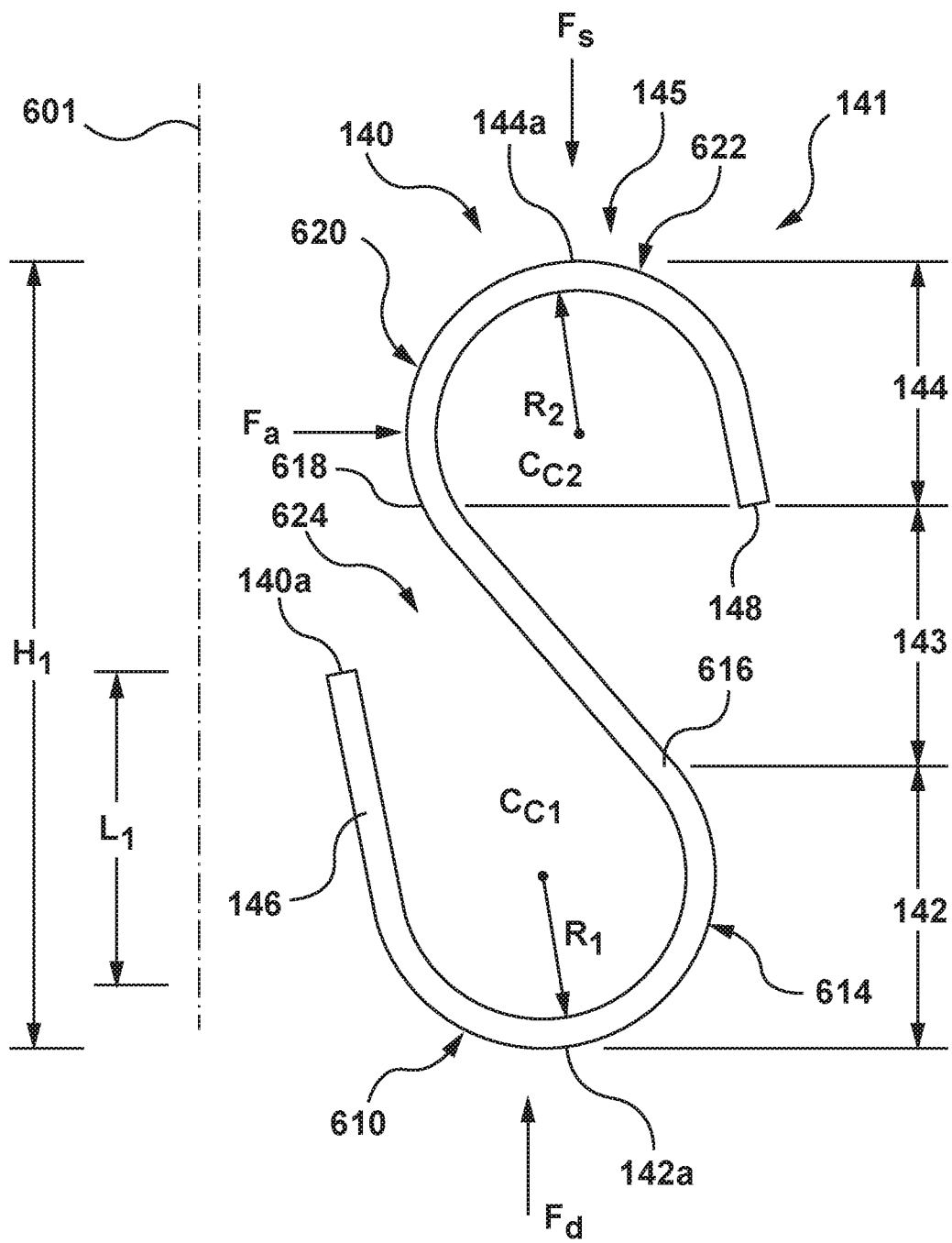
Figure 7:
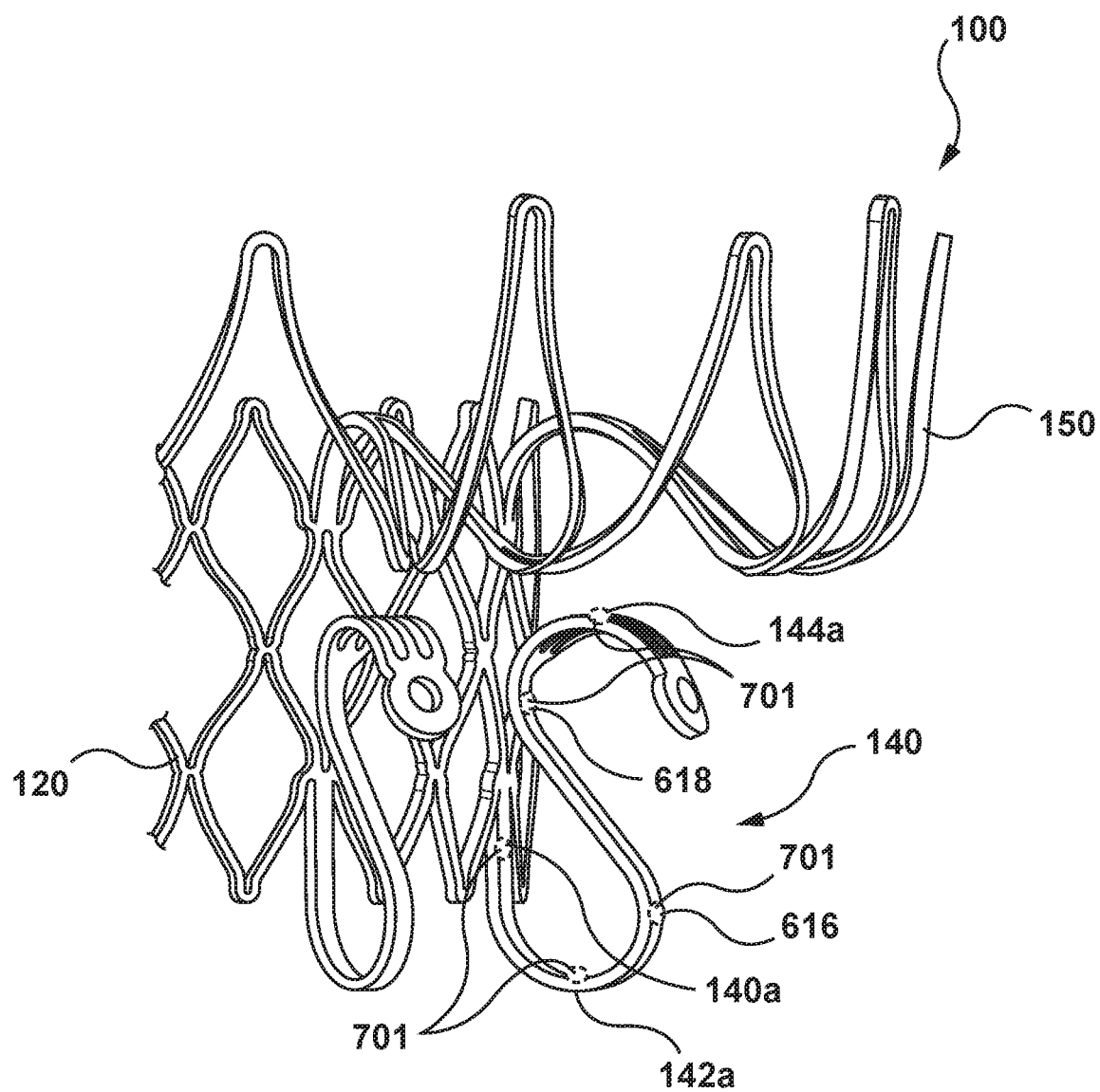
FIG. 7 is a partial side view of a heart valve prosthesis showing a plurality of flexible regions on a support arm in accordance with an embodiment of the present technology.

FIGS. 6A-6C are side views of a variety of support arm configurations in accordance with additional embodiments of the present technology. Referring to FIGS. 6A-6C together, the support arm 140, in one embodiment, can generally have the curvilinear shape 141 with first and second arcuate regions 142, 144 separated by an elongate or substantially straight region 143 that together extend substantially in parallel with a longitudinal axis 601 (e.g., generally aligned with the longitudinal axis $L_a$ of the valve support 120; FIG. 5B). In some embodiments, the support arm 140 has an S-shaped profile. As illustrated in FIGS. 6A-6C, the first arcuate region 142 can have a first radius of curvature $R_1$ and the second arcuate region 144 can have a second radius of curvature $R_2$ that, in certain embodiments, is (a) substantially equal to the first radius of curvature $R_1$ (FIG. 6A), (b) substantially less than the first radius of curvature $R_1$ (FIG. 6B), or is (c) substantially greater than the first radius of curvature $R_1$ (FIG. 6C).

Referring to FIGS. 5B and 6A-6C together, the second arcuate region 144 can have the tissue engaging portion or contact zone 145 for engaging subannular or other cardiac tissue during and/or after deployment. In the embodiments illustrated in FIGS. 6A-6D, the support arm 140 includes the arm post 146 at a first end 140a and from which the first arcuate region 142 generally extends in the outward direction from the longitudinal axis $L_A$, 601 and in radial alignment with the downstream portion 126 of the valve support 120 (FIG. 5B). The first arcuate region 142 curves about a first center of curvature $C_{C1}$. As shown in FIG. 6A, the substantially straight or elongate portion 143 extends between the first arcuate region 142 and the second arcuate region 144. The second arcuate region 144 is radially aligned with an intermediate or middle portion 170 of the valve support 120 between the upstream and downstream portions 124, 126 (FIG. 5B). In one embodiment, the second arcuate region 144 curves about a second center of curvature $C_{C2}$. In the embodiments illustrated in FIGS. 5B and 6A-6C, a first axis line (not shown) drawn through the first center of curvature $C_{C1}$ is parallel to a second axis line (not shown) drawn through the second center of curvature $C_{C2}$. The first and second axis lines are substantially perpendicular to the longitudinal axis $L_A$, 601 (FIG. 6A).

Referring to FIG. 6A, and in some embodiments, the arm post 146 can be generally linear and have a suitable length $L_1$ for extending the first arcuate region 142 a desirable distance downstream from a connection (not shown) to the valve support 120. In some embodiments, the arm post 146 can be generally parallel to the longitudinal axis $L_A$ of the prosthesis 100 and/or valve support 120 (shown in FIG. 5B). Following the general curvature of the first arcuate region 142 shown in FIG. 6A, a first curved segment 610 of the region 142 extends radially outward from the arm post 146. More particularly, the first curved segment 610 may be described as arcuate or generally curved in an outward and downstream direction until it reaches a transitional apex 142a of the first arcuate region 142. Thereafter a second curved segment 614 of the first arcuate region 142 continues the curve profile and extends outward and in a generally upstream direction from the transitional apex 142a.

As shown in FIG. 6A, a first transitional point 616 initiates the elongate region 143 of the support arm 140, with the elongate region 143 slanting and extending in an upward and inward direction relative to the longitudinal axis $L_A$ of the valve support 120 to end at a second transitional point 618. In similar fashion, the general curvature of the second arcuate region 144 initiates as the second transitional point 618 such that following the curvature of the second arcuate region 144, a third curved segment 620 is defined that generally curves in an outward and upstream direction to reach a transitional apex 144a of the second arcuate region 144. A fourth curved segment 622 of the second arcuate region 144 continues the curve profile and extends (e.g., relative to the longitudinal axis $L_A$) from the transitional apex 144a in an outward direction and can also curve slightly downstream toward a free-end or arm tip 148. An opening 624 between the second arcuate region 144 and the first arcuate region 142 of the support arm 140 is generally created in the space between the third transition 618 and the first end 140a of the support arm 140, and can be configured to receive a native leaflet LF and/or chordae tendinae therein. Other embodiments of support arms 140 can have curved segments 610, 614, 620 and 622 with less curvature or greater curvature. Additionally, the embodiments of support arms 140 shown in FIGS. 5B and 6A-6D can have an overall height $H_1$ that is less than a height $H_2$ of the valve support 120 (FIGS. 5B and 6A). Other arrangements and heights are also contemplated. Accordingly, in addition to the radius of curvature $R_1$, $R_2$ of the first and second arcuate regions 142, 144 and/or other geometric features/alterations, the overall height $H_1$ of the support arm 140 can be selected to accommodate the anatomy at the desired target location of the heart valve.

Referring again to FIG. 6A, the first and second arcuate regions 142, 144 of the support arm 140 can be configured to absorb, translate and/or mitigate distorting forces present within the heart during, for example, systole and diastole. In particular arrangements, the support arms 140 have a spring-type response to distorting forces (e.g., physical forces capable of exerting on and changing a contour of the support arm 140). As described in more detail herein, the support arms 140 can have multiple hinge points for flexing or absorbing such distorting forces. For example, a first distorting force can be absorbed as a result of the spring-type response of the individual support arms 140 in a manner that elastically or reversibly and temporarily distorts the unbiased configuration of the support arm 140. As the first distorting force dissipates (e.g., during the cardiac cycle), the spring-type motion continues with the transition of the support arm contour from the distorted position back to an unbiased configuration. Accordingly, a spring-type response of the support arm 140 occurs in a manner that is counter to the first distorting force. In these arrangements, the extent to which the support arm 140 is compressed and/or extended is proportional to the distorting force(s) exerted on the support arm. The support arm 140 can have a selected stiffness which provides a constant for the distance or delta of distortion (e.g., compression, distention). In certain arrangements, the support arms 140 can have constant stiffness along the entire length of the support arm and covering all of the multiple hinge points. In other arrangements, the support arms 140 can have variable stiffness along the length of the support arm and encompassing the different hinge points. Such selectivity in the stiffness of the individual support arms 140 can provide prosthesis designs to accommodate unique and variable native structures, such as for accommodating variable distorting forces exerted by the native mitral valve region. Variable stiffness may be accomplished in a variety of ways: i) differences in the support arm cross-sectional area, ii) variable cold working of select support arms in the case of conventional elastic-plastic metals (e.g. stainless steel, titanium alloys, cobalt-chromium based alloys), and/or iii) selectively heating or providing a heat treatment of one or more support arms and not others.

In particular embodiments, the shape and/or size of the first and second arcuate regions 142, 144 can be selected to accommodate forces, such as radially compressive forces, e.g., exerted by the native annulus and/or leaflets Fa, longitudinal diastolic Fd and systolic Fs forces, hoop stress, etc. Absorption of the distorting forces can serve to prevent translation of those forces to the valve support 120 and thereby preserve the coaptation of the prosthetic valve component 130. Additionally, and as further shown in FIG. 7, absorption of the distorting forces along the entirety of the support arm 140 and/or at several hinge points or locations 701 (e.g., transitions 140a, 142a, 616, 618 and 144a) distribute the stress caused by the forces, thereby substantially preventing fatigue of the support arms 140 and/or minimizing tissue erosion at contacted portions of the native anatomy. In accordance with the present technology, the support arms 140 may flex, bend, rotate or twist under the distorting forces while the valve support 120 substantially maintains its rigidity and/or original shape (e.g., a generally circular shape).

FIGS. 8A-8H are side views of various support arms 140 flexing in response to a distorting force in accordance with further embodiments of the present technology. The degree of flexibility of individual support arms 140 may be consistent among all support arms 140 of a prosthesis 100, or, alternatively, some support arms 140 may be more flexible than other support arms 140 on the same prosthesis 100. Likewise, a degree of flexibility of individual support arms 140 may be consistent throughout an entire length of the support arm 140 or curvature of the first and second arcuate regions 142, 144. In other embodiments, however, the degree of flexibility can vary along the length and/or curvature of each support arm 140.

Figure 8A:
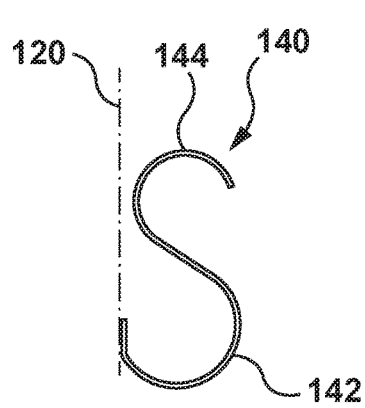
FIGS. 8A-8H are side views of various support arms flexing in response to a distorting force in accordance with further embodiments of the present technology.
Figure 8B:
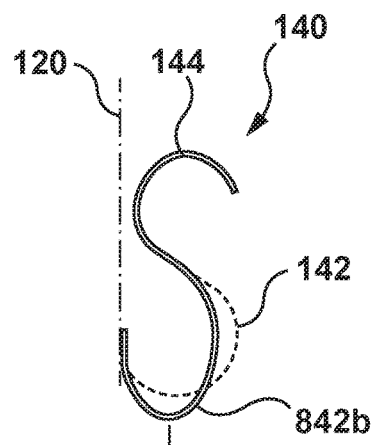
Figure 8C:
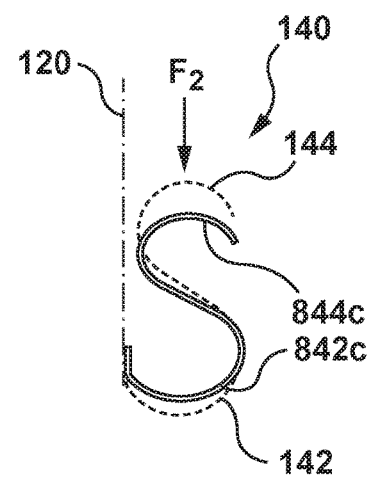
Figure 8D:
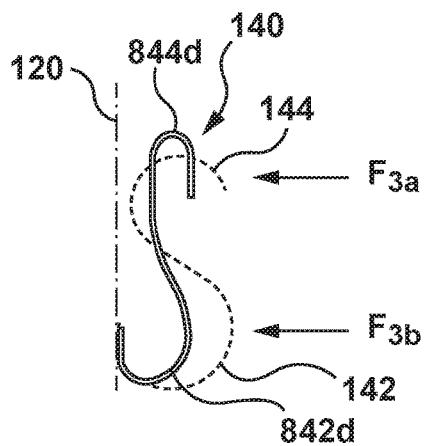
Figure 8E:
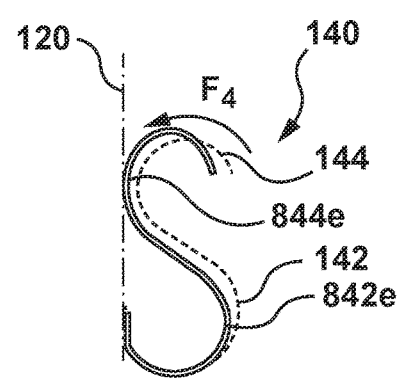

As shown FIGS. 8A-8H, the first and second arcuate regions 142, 144 of the support arms 140 may flex relative to the arm post 146, the valve support 120 (shown in dotted lines) and/or be configured to alter their arcuate shape(s) in response to varying distorting forces F that can be applied by the surrounding tissue during or after implantation of the prosthesis 100. From a static position (FIG. 8A), the first arcuate region 142 may flex downward to a shape/position 842b (FIG. 8B) in response to a downward force $F_1$ caused by, for example, chordal load (e.g., from chordal tendinae engaging the first arcuate region 142). In another embodiment, the second arcuate region 144 may flex downward and the first arcuate region 142 may compress from the static position (FIG. 8A) to shapes/positions 844c and 842c, respectively (FIG. 8C), in response to a downward force $F_2$ caused by, for example, a tip load (e.g., from left ventricle pressure). Similarly, the first and second arcuate regions 142, 144 may flex or compress inward to shapes/positions 842d, 844d (FIG. 8D) in response to laterally directed inward forces $F_{3a}$, $F_{3b}$ caused by, for example, ventricle wall load (e.g., from left ventricle contraction). Engagement of the native annulus by the second arcuate region 144, resulting in force $F_4$, may flex and compress the second arcuate region 144 inward to shape/position 844e, which may also promote a position change in the first arcuate region to position 842e (FIG. 8E). In some embodiments, the first and second arcuate regions 142, 144 may flex, rotate inwardly/outwardly and/or deform in response to the laterally directed forces $F_{3a}$, $F_{3b}$, $F_4$, or downward in response to the generally vertically directed forces $F_1$, $F_2$.

Figure 8F:
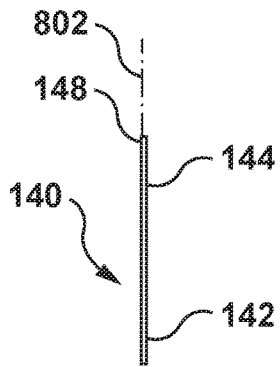
Figure 8G:
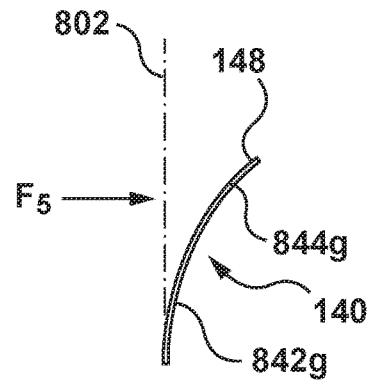
Figure 8H:
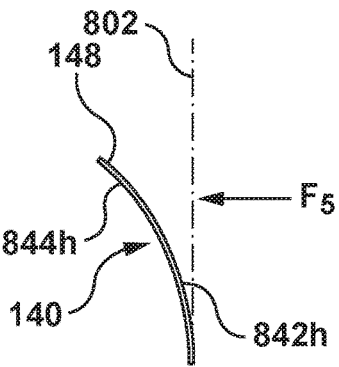

In other arrangements, and as shown in FIGS. 8F-8H, the first and second arcuate regions 142, 144 shown in a static position in FIG. 8F may also flex and/or rotate laterally, for example, to positions 842g/844g (FIG. 8G) or 842h/844h (FIG. 8H) in response to a laterally-directed force $F_5$, by bending at one or more transitions 140a, 142a, 616, 618 and 144a (FIG. 6A), for example, at unique and variable angles off a midline 802 such that the arm tips 148 may be splayed away from each other.

Figures 9, 10:
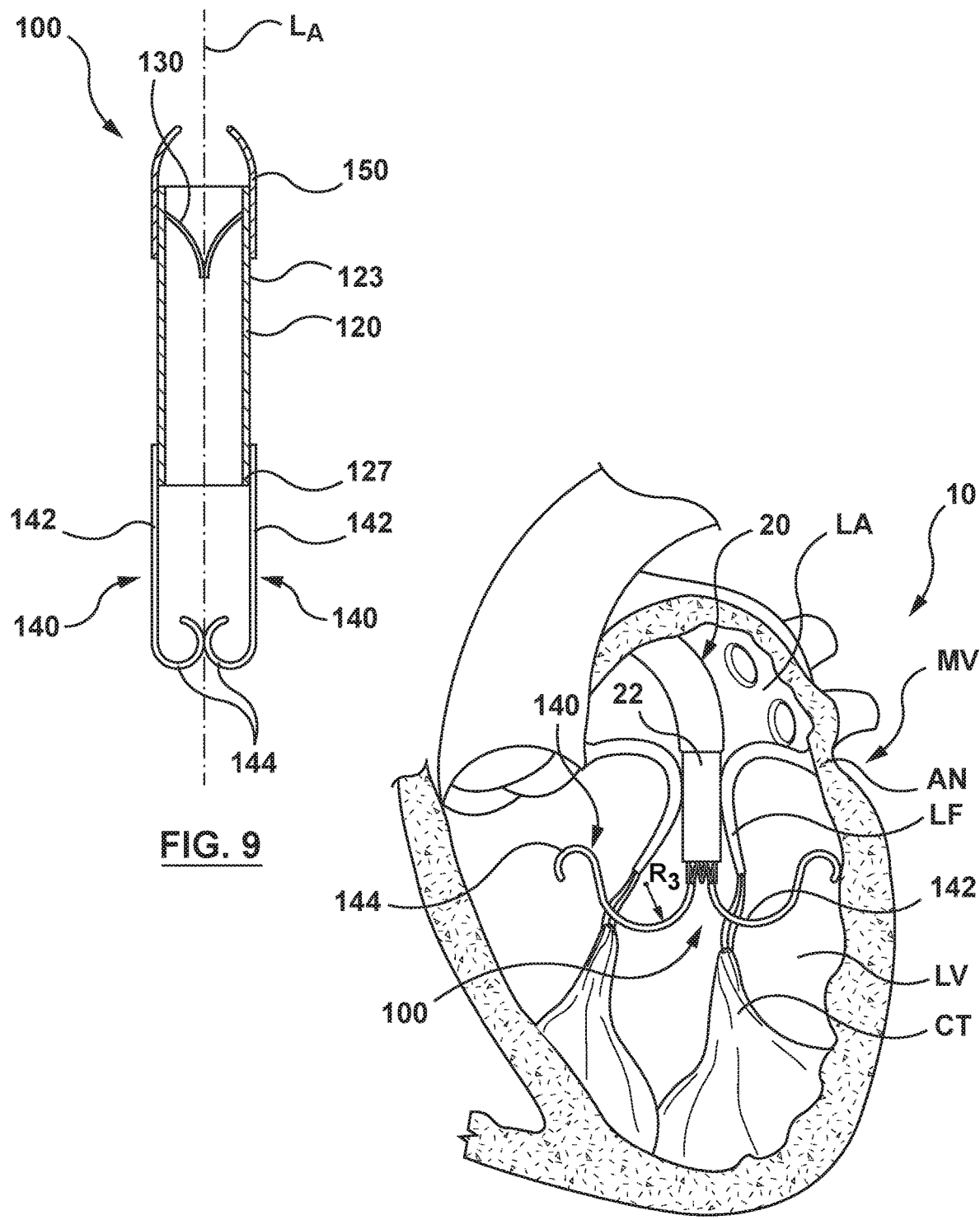
FIG. 9 is an enlarged sectional view of the heart valve prosthesis of FIGS. 5A-5B shown in a delivery configuration (e.g., low-profile or radially compressed state) in accordance with an embodiment of the present technology.
FIG. 10 is a sectional view of the heart illustrating a step of a method of implanting a heart valve prosthesis using a trans-septal approach in accordance with another embodiment of the present technology.

FIG. 9 is an enlarged sectional view of the heart valve prosthesis 100 of FIGS. 5A-5B shown in a compressed delivery configuration (e.g., a low-profile or radially compressed state) configured in accordance with an embodiment of the present technology. The prosthesis 100 can be configured for delivery within a delivery catheter sheath (not shown) in the radially compressed configuration shown in FIG. 9. More particularly, in the radially compressed configuration, the radially-extending segment 150 can be elongated, folded or otherwise arranged to longitudinally extend in a substantially straightened state from the valve support 120. Additionally, the plurality of support arms 140 are longitudinally extended and arranged in a substantially straightened state for percutaneous delivery to the targeted native heart valve. As shown in FIG. 9, the support arms 140 can extend beyond the second end 127 of the valve support 120 such that the first arcuate region 142 is generally linear and substantially parallel with the longitudinal axis $L_A$, while the second arcuate region 144 remains in a curved profile. Upon release of the radial constraint, the support arms 140 can move to an outward biased position as the delivery catheter sheath (not shown) is withdrawn and the radially-extending segment 150 can self-expand to the radially expanded configuration (FIG. 5B). Additionally, in the event that the heart valve prosthesis 100 needs to be repositioned, removed and/or replaced after implantation, the radially-extending segment 150 and the valve support 120 can transition from the radially expanded configuration (e.g., the deployed state) (FIG. 5B) back to the radially contracted configuration (FIG. 9) using a catheter device or other lateral retaining sheath.

Access to the mitral valve or other atrioventricular valve can be accomplished through a patient's vasculature in a percutaneous manner. Depending on the point of vascular access, the approach to the mitral valve may be antegrade and may rely on entry into the left atrium by crossing the inter-atrial septum. Alternatively, approach to the mitral valve can be retrograde where the left ventricle is entered through the aortic valve or via a transapical puncture. Once percutaneous access is achieved, the interventional tools and supporting catheter(s) may be advanced to the heart intravascularly and positioned adjacent the target cardiac valve in a variety of manners. For example, the heart valve prosthesis 100 may be delivered to a native mitral valve region for repair or replacement of the native valve via a transseptal approach (shown in FIG. 10), a retrograde approach through the aortic valve, or via a transapical puncture. Suitable transapical and/or transatrial implantation procedures that may be adapted for use with the heart valve prostheses 100 described herein are disclosed in U.S. application Ser. No. 13/572,842 filed Aug. 13, 2012 to Igor Kovalsky, U.S. Appl. Pub. No. 2011/0208297 to Tuval et al., and U.S. Appl. Pub. No. 2012/0035722 to Tuval et al, each of which is incorporated by reference herein in its entirety.

FIG. 10 is a sectional view of the heart 10 illustrating a step of a method of implanting a heart valve prosthesis 100 using a transseptal approach in accordance with another embodiment of the present technology. Referring to FIGS. 5A, 9 and 10 together, the prosthesis 100 may be advanced into proximity to the mitral valve MV within a delivery catheter 20. Optionally, a guidewire (not shown) may be used over which the delivery catheter 20 may be slidably advanced. A sheath 22 of the delivery catheter 20, which contains the prosthesis 100 in a radially compressed configuration (shown in FIG. 9), is advanced through the mitral valve annulus AN between native leaflets LF, as shown in FIG. 10. Referring to FIG. 10, the sheath 22 is then proximally retracted allowing the prosthesis 100 to expand such that the support arms 140 are in an outward position spatially separated from the longitudinal axis $L_A$ and while the valve support 120 remains radially contracted. In this deployment phase, the outward movement of the support arms 140 is facilitated by the shape-memory bias of the first arcuate region 142. In this transition phase, the first arcuate region 142 can have a third radius of curvature $R_3$ that is greater than the first radius of curvature $R_1$, whereas the second arcuate region 144 continues to have the second radius of curvature $R_2$. The second arcuate region 144 provides for atraumatic engagement of cardiac tissue during all phases of deployment within the Mitral Valve MV (as shown in FIG. 10). For example, the second arcuate region 144 is configured to deflect in response to contact with chordae tendinae CT when transitioning between the radially contracted configuration and the radially expanded configuration. The second arcuate region 144 can also atraumatically engage a wall of the left ventricle LV during deployment and as the support arm 140 moves or swings behind the native leaflets LF. When the support arms 140 are fully deployed (e.g., FIG. 5A), the support arms 140 are positioned further inwardly relative to the longitudinal axis $L_A$ and such that the leaflets LF are engaged between the support arms 140 and the valve support 120. The sheath 22 may be further retracted to release the valve support 120 and the radially-extending segment 150 (e.g., within the space of the left atrium LA).

After the sheath 22 has been removed and the prosthesis 100 allowed to return to its deployed state, the delivery catheter 20 can still be connected to the prosthesis 100 (e.g., system eyelets, not shown, are connected to the prosthesis eyelets) so that the operator can further control the placement of the prosthesis 100 as it expands toward the radially expanded configuration. For example, the prosthesis 100 may be expanded upstream or downstream of the target location then pushed downstream or upstream, respectively, into the desired target location before releasing the prosthesis 100 from delivery catheter 20. Once the prosthesis 100 is positioned at the target site, the delivery catheter 20 may be retracted in a proximal direction and the prosthesis 100 detached while in the radially expanded configuration at the native target valve (e.g., mitral valve MV).

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A heart valve repair device, comprising:
    a frame comprising
        a support having an upstream portion configured to be positioned proximate to a left atrium, a downstream portion configured to be positioned proximate to a left ventricle, and a first cross-sectional dimension;
        a radially-extending segment extending from the upstream portion of the support and having a second cross-sectional dimension greater than the first cross-sectional dimension, the radially-extending segment having a first arcuate section curving downwardly in a downstream direction and a second arcuate section extending from the first arcuate section and curving upwardly in an upstream direction, wherein the radially-extending segment is configured to engage cardiac tissue of the left atrium; and
        a support arm extending from the downstream portion of the support, wherein, when the heart valve repair device is in an expanded configuration,
            the support arm extends radially outwardly from the downstream portion and back toward the upstream portion of support,
            the support arm is configured to extend behind a native leaflet of a native mitral valve and engage subannular tissue within the left ventricle, and
            the support arm has a curvilinear shape with opposing first and second arcuate regions longitudinally separated by a substantially straight region extending therebetween, the first arcuate region extending from the downstream portion of the support and curved toward the support, the substantially straight region slanting inward toward the support relative to a longitudinal axis of the support and joining the first and second arcuate regions, and the second arcuate region curving outwardly away from the support proximate to the upstream portion, the second arcuate portion being configured to atraumatically engage subannular tissue behind the native leaflet,
    wherein the support includes a plurality of struts that define a plurality of diamond-shaped openings, and the support arm includes a first end that includes all attachments formed between the support arm and the support and a second end opposing the first end, the first end of the support arm being coupled to the support via at least one attachment point and the second end being radially spaced apart from the support, the first end having a first width that spans less than a single diamond-shaped opening of the plurality of diamond-shaped openings of the support,
    wherein the second arcuate portion of the support arm has a landing zone configured to atraumatically engage the subannular tissue behind the native leaflet, and wherein the landing zone has a width greater than a width of other portions of the support arm and wherein the landing zone is disposed radially inward of the second end of the support arm.

2. The heart valve repair device of claim 1, wherein the first arcuate region, the second arcuate region, and the substantially straight region together define a substantially S-shape.

3. The heart valve repair device of claim 1, wherein the second arcuate region defines a first curved segment that curves in an outward and upstream direction from a transitional point to reach an apex of the support arm, and wherein the second arcuate region further defines a second curved segment that extends in an outward direction from the apex and curves slightly downward to a free-end of the support arm.

4. The heart valve repair device of claim 1, wherein the radially extending segment comprises a plurality of interconnected struts extending radially outwardly from the upstream portion of the support and in an upstream direction away from the support and where the radially-extending segment forms an atraumatic end portion.

5. A heart valve repair device, comprising:
    a frame comprising
        a support having an upstream portion configured to be positioned proximate to a left atrium, a downstream portion configured to be positioned proximate to a left ventricle, and a first cross-sectional dimension; and a support arm extending from the downstream portion of the support, wherein, when the heart valve repair device is in an expanded configuration, the support arm extends radially outwardly from the downstream portion and back toward the upstream portion of support, the support arm is configured to extend behind a native leaflet of a native mitral valve and engage subannular tissue within the left ventricle, and the support arm has a curvilinear shape with opposing first and second arcuate regions longitudinally separated by a substantially straight region extending therebetween, the first arcuate region extending from the downstream portion of the support and curved toward the support, the substantially straight region slanting inward toward the support relative to a longitudinal axis of the support and joining the first and second arcuate regions, and the second arcuate region curving outwardly away from the support proximate to the upstream portion, the second arcuate portion being configured to atraumatically engage subannular tissue behind the native leaflet, wherein the support includes a plurality of struts that define a plurality of diamond-shaped openings, and the support arm includes a first end that includes all attachments formed between the support arm and the support and a second end opposing the first end, the first end of the support arm being coupled to the support via at least one attachment point and the second end being radially spaced apart from the support, the first end having a first width that spans less than a single diamond-shaped opening of the plurality of diamond-shaped openings of the support, wherein the second arcuate portion of the support arm has a landing zone configured to atraumatically engage the subannular tissue behind the native leaflet, and wherein the landing zone has a width greater than a width of other portions of the support arm and wherein the landing zone is disposed radially inward of the second end of the support arm.

6. The heart valve repair device of claim 5, wherein the first arcuate region, the second arcuate region, and the substantially straight region together define a substantially S-shape.

7. The heart valve repair device of claim 5, wherein the second arcuate region defines a first curved segment that curves in an outward and upstream direction from a transitional point to reach an apex of the support arm, and wherein the second arcuate region further defines a second curved segment that extends in an outward direction from the apex and curves slightly downward to a free-end of the support arm.

\* \* \* \* \*